United States Patent
Plos et al.

(10) Patent No.: US 7,192,454 B2
(45) Date of Patent: Mar. 20, 2007

(54) COMPOSITION FOR DYEING HUMAN KERATIN MATERIALS, COMPRISING A FLUORESCENT DYE AND A PARTICULAR SEQUESTERING AGENT, PROCESS THEREFOR AND USE THEREOF

(75) Inventors: Grégory Plos, Paris (FR); Luc Gourlaouen, Asnieres (FR)

(73) Assignee: L'Oreal S.A., Paris (FR)

( * ) Notice: Subject to any disclaimer, the term of this patent is extended or adjusted under 35 U.S.C. 154(b) by 310 days.

(21) Appl. No.: 10/814,585

(22) Filed: Apr. 1, 2004

(65) Prior Publication Data

US 2005/0098763 A1    May 12, 2005

Related U.S. Application Data

(60) Provisional application No. 60/468,081, filed on May 6, 2003.

(30) Foreign Application Priority Data

Apr. 1, 2003   (FR)   ................... 03 04024

(51) Int. Cl.
*A61K 7/13*   (2006.01)
(52) U.S. Cl. ................ 8/405; 8/406; 8/407; 8/410; 8/411; 8/421; 8/594; 8/648; 132/202; 132/208
(58) Field of Classification Search .............. 8/405, 8/406, 407, 410, 411, 421, 594, 648; 132/202, 132/208
See application file for complete search history.

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Ditmar |
| 2,375,853 A | 5/1945 | Kirby et al. |
| 2,388,614 A | 11/1945 | Kirby et al. |
| 2,454,547 A | 11/1948 | Bock et al. |
| 2,798,053 A | 7/1957 | Brown |
| 2,851,424 A | 9/1958 | Switzer et al. |
| 2,923,692 A | 2/1960 | Ackerman et al. |
| 2,961,347 A | 11/1960 | Floyd |
| 2,979,465 A | 4/1961 | Parran et al. |
| 3,014,041 A | 12/1961 | Hausermann et al. |
| 3,206,462 A | 9/1965 | McCarty |
| 3,227,615 A | 1/1966 | Korden |
| 3,472,840 A | 10/1969 | Stone et al. |
| 3,632,559 A | 1/1972 | Matter et al. |
| 3,639,127 A | 2/1972 | Brooker et al. |
| 3,658,985 A | 4/1972 | Olson, Jr. et al. |
| 3,856,550 A | 12/1974 | Bens et al. |
| 3,874,870 A | 4/1975 | Green et al. |
| 3,910,862 A | 10/1975 | Barabas et al. |
| 3,912,808 A | 10/1975 | Sokol |
| 3,915,921 A | 10/1975 | Schlatzer, Jr. |
| 3,917,817 A | 11/1975 | Vanlerberghe et al. |
| 3,929,990 A | 12/1975 | Green et al. |
| 3,966,904 A | 6/1976 | Green et al. |
| 3,986,825 A | 10/1976 | Sokol |
| 4,001,432 A | 1/1977 | Green et al. |
| 4,005,193 A | 1/1977 | Green et al. |
| 4,013,787 A | 3/1977 | Varlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,075,136 A | 2/1978 | Schaper |
| 4,131,576 A | 12/1978 | Iovine et al. |
| 4,157,388 A | 6/1979 | Christiansen |
| 4,165,367 A | 8/1979 | Chakrabarti |
| 4,166,894 A | 9/1979 | Schaper |
| 4,172,887 A | 10/1979 | Vanlerberghe et al. |
| 4,185,087 A | 1/1980 | Morlino |
| 4,189,468 A | 2/1980 | Vanlerberghe et al. |
| 4,197,865 A | 4/1980 | Jacquet et al. |
| 4,217,914 A | 8/1980 | Jacquet et al. |
| 4,223,009 A | 9/1980 | Chakrabarti |

(Continued)

FOREIGN PATENT DOCUMENTS

AT          302 534         10/1972

(Continued)

OTHER PUBLICATIONS

CAS Abstract for JP 2000-136340—Chemical Abstracts Service, Database Accession No. 2000: 317079; XP-002269220, JP 2000136340 (Pentel Co., Ltd.), May 16, 2000.

(Continued)

*Primary Examiner*—Eisa Elhilo
(74) *Attorney, Agent, or Firm*—Finnegan, Henderson, Farabow, Garrett & Dunner, L.L.P.

(57) ABSTRACT

The invention relates to a composition comprising at least one fluorescent dye and at least one particular sequestering agent, and also to processes and a device for using these compositions.

The invention similarly relates to the use of a composition comprising at least one particular fluorescent dye and at least one particular sequestering agent, to dye with a lightening effect human keratin materials and more particularly artificially dyed or pigmented hair, and colored skin.

31 Claims, No Drawings

U.S. PATENT DOCUMENTS

| | | |
|---|---|---|
| 4,237,243 A | 12/1980 | Quack et al. |
| 4,240,450 A | 12/1980 | Grollier et al. |
| 4,256,458 A | 3/1981 | Degen et al. |
| 4,277,581 A | 7/1981 | Vanlerberghe et al. |
| 4,381,919 A | 5/1983 | Jacquet et al. |
| 4,422,853 A | 12/1983 | Jacquet et al. |
| 4,445,521 A | 5/1984 | Grollier et al. |
| 4,509,949 A | 4/1985 | Huang et al. |
| 4,591,610 A | 5/1986 | Grollier |
| 4,608,250 A | 8/1986 | Jacquet et al. |
| 4,693,935 A | 9/1987 | Mazurek |
| 4,702,906 A | 10/1987 | Jacquet et al. |
| 4,719,099 A | 1/1988 | Grollier et al. |
| 4,719,282 A | 1/1988 | Nadolsky et al. |
| 4,728,571 A | 3/1988 | Clemens et al. |
| 4,761,273 A | 8/1988 | Grollier et al. |
| 4,781,724 A | 11/1988 | Wajaroff et al. |
| 4,823,985 A | 4/1989 | Grollier et al. |
| 4,839,166 A | 6/1989 | Grollier et al. |
| 4,948,579 A | 8/1990 | Jacquet et al. |
| 4,961,925 A | 10/1990 | Tsujino et al. |
| 4,972,037 A | 11/1990 | Garbe et al. |
| 4,996,059 A | 2/1991 | Grollier et al. |
| 5,009,880 A | 4/1991 | Grollier et al. |
| 5,057,311 A | 10/1991 | Hanazawa et al. |
| 5,089,252 A | 2/1992 | Grollier et al. |
| 5,139,037 A | 8/1992 | Grollier et al. |
| 5,188,639 A | 2/1993 | Schultz et al. |
| 5,196,189 A | 3/1993 | Jacquet et al. |
| 5,275,808 A | 1/1994 | Murray et al. |
| 5,356,438 A | 10/1994 | Kim et al. |
| 5,445,655 A | 8/1995 | Kuhn et al. |
| 5,635,461 A | 6/1997 | Onitsuka et al. |
| 5,708,151 A | 1/1998 | Möckli |
| 5,733,343 A | 3/1998 | Mockli |
| 5,744,127 A | 4/1998 | Giuseppe et al. |
| 5,792,221 A | 8/1998 | Lagrange et al. |
| 5,830,446 A | 11/1998 | Berthiaume et al. |
| 5,833,997 A | 11/1998 | Mahieu et al. |
| 5,853,708 A | 12/1998 | Cauwet et al. |
| 5,873,494 A | 2/1999 | Dallas, Jr. |
| 5,958,392 A | 9/1999 | Grollier et al. |
| 5,961,667 A * | 10/1999 | Doehling et al. ............... 8/408 |
| 5,962,522 A | 10/1999 | Wacher et al. |
| 6,106,577 A | 8/2000 | Audousset et al. |
| 6,120,780 A | 9/2000 | Dupuis et al. |
| 6,180,666 B1 | 1/2001 | Wacher et al. |
| 6,260,556 B1 | 7/2001 | Legrand et al. |
| 6,375,958 B1 | 4/2002 | Cauwet et al. |
| 6,391,062 B1 | 5/2002 | Vandenbossche et al. |
| 6,436,151 B2 | 8/2002 | Cottard et al. |
| 6,436,153 B2 | 8/2002 | Rondeau |
| 6,475,248 B2 | 11/2002 | Ohashi et al. |
| 6,570,019 B2 | 5/2003 | Pasquier et al. |
| 6,576,024 B1 | 6/2003 | Lang et al. |
| 6,592,630 B2 | 7/2003 | Matsunaga et al. |
| 6,616,709 B2 | 9/2003 | Ohashi et al. |
| 6,712,861 B2 | 3/2004 | Rondeau |
| 2001/0010812 A1 | 8/2001 | Chevalier et al. |
| 2001/0023514 A1 | 9/2001 | Cottard et al. |
| 2001/0023515 A1 | 9/2001 | Cottard et al. |
| 2001/0031270 A1 | 10/2001 | Douin et al. |
| 2001/0034914 A1 | 11/2001 | Saunier et al. |
| 2001/0054206 A1 * | 12/2001 | Matsunaga et al. ............ 8/405 |
| 2001/0055580 A1 | 12/2001 | Belli et al. |
| 2002/0004956 A1 | 1/2002 | Rondeau |
| 2002/0012681 A1 | 1/2002 | George et al. |
| 2002/0026676 A1 | 3/2002 | Ohashi et al. |
| 2002/0046431 A1 | 4/2002 | Laurent et al. |
| 2002/0046432 A1 | 4/2002 | Rondeau |
| 2002/0088063 A1 | 7/2002 | Ohashi et al. |
| 2002/0131941 A1 | 9/2002 | Habeck et al. |
| 2002/0176836 A9 | 11/2002 | Belli et al. |
| 2002/0176875 A9 | 11/2002 | Douin et al. |
| 2003/0000023 A9 | 1/2003 | Rondeau |
| 2003/0019052 A1 | 1/2003 | Pratt |
| 2003/0019053 A9 | 1/2003 | Rondeau |
| 2003/0055268 A1 | 3/2003 | Pasquier et al. |
| 2003/0074747 A1 | 4/2003 | Vuarier et al. |
| 2003/0124079 A1 | 7/2003 | Mougin et al. |
| 2003/0131424 A1 | 7/2003 | Audousset et al. |
| 2004/0019981 A1 | 2/2004 | Cottard et al. |
| 2004/0034945 A1 | 2/2004 | Javet et al. |
| 2004/0037796 A1 | 2/2004 | Cottard et al. |
| 2004/0049860 A1 | 3/2004 | Cottard et al. |
| 2004/0105830 A1 * | 6/2004 | Boswell et al. ............ 424/70.2 |
| 2004/0141943 A1 | 7/2004 | Mougin et al. |
| 2004/0148711 A1 | 8/2004 | Rondeau |
| 2004/0205901 A1 | 10/2004 | Cottard et al. |
| 2004/0258641 A1 | 12/2004 | Plos et al. |
| 2005/0005368 A1 | 1/2005 | Plos et al. |
| 2005/0005369 A1 | 1/2005 | Plos et al. |
| 2005/0008593 A1 | 1/2005 | Plos et al. |
| 2005/0028301 A1 | 2/2005 | Pastore |
| 2005/0144741 A1 | 7/2005 | Lang et al. |

FOREIGN PATENT DOCUMENTS

| | | |
|---|---|---|
| CA | 1255603 | 6/1989 |
| CH | 487 231 | 3/1970 |
| DE | 33 13 332 | 10/1984 |
| DE | 196 46 804 A1 | 5/1997 |
| DE | 199 23 438 A1 | 11/2000 |
| DE | 199 26 377 A1 | 12/2000 |
| DE | 100 29 441 A1 | 1/2002 |
| DE | 101 41 683 A1 | 6/2003 |
| DE | 101 48 844 A1 | 10/2003 |
| EP | 0 087 060 B1 | 8/1983 |
| EP | 0 095 238 A2 | 11/1983 |
| EP | 0 080 976 B1 | 9/1986 |
| EP | 0 173 109 | 10/1989 |
| EP | 0 370 470 B1 | 5/1990 |
| EP | 0 412 704 B1 | 2/1991 |
| EP | 0 412 707 B1 | 2/1991 |
| EP | 0 445 342 B1 | 9/1991 |
| EP | 0 486 135 B1 | 5/1992 |
| EP | 0 122 324 B2 | 2/1993 |
| EP | 0 337 354 B1 | 2/1994 |
| EP | 0 582 152 B1 | 2/1994 |
| EP | 0 395 282 | 3/1995 |
| EP | 0 503 853 | 5/1996 |
| EP | 0 714 954 A2 | 6/1996 |
| EP | 0 733 355 A2 | 9/1996 |
| EP | 0 815 828 B1 | 6/1999 |
| EP | 0 970 684 A1 | 1/2000 |
| EP | 1 023 891 B1 | 8/2000 |
| EP | 1 099 437 | 5/2001 |
| EP | 1 132 076 A1 | 9/2001 |
| EP | 1 133 977 A2 | 9/2001 |
| EP | 1 191 041 A2 | 3/2002 |
| FR | 1492597 | 9/1966 |
| FR | 1583363 | 10/1969 |
| FR | 2077143 | 10/1971 |
| FR | 2080759 | 11/1971 |
| FR | 2103210 | 7/1972 |
| FR | 2162025 | 7/1973 |
| FR | 2190406 | 2/1974 |
| FR | 2252840 | 6/1975 |
| FR | 2270846 | 12/1975 |
| FR | 2280361 | 2/1976 |
| FR | 2316271 | 1/1977 |
| FR | 2320330 | 3/1977 |
| FR | 2336434 | 7/1977 |
| FR | 2368508 | 5/1978 |

| | | |
|---|---|---|
| FR | 2383660 | 10/1978 |
| FR | 2393573 | 1/1979 |
| FR | 2411219 | 7/1979 |
| FR | 2416723 | 9/1979 |
| FR | 2470596 | 6/1981 |
| FR | 2505348 | 11/1982 |
| FR | 2519863 | 7/1983 |
| FR | 2542997 | 9/1984 |
| FR | 2586913 | 3/1987 |
| FR | 2589476 | 5/1987 |
| FR | 2598611 | 11/1987 |
| FR | 2692572 | 6/1992 |
| FR | 2741261 | 5/1997 |
| FR | 2 773 470 | 7/1999 |
| FR | 2 773 864 | 7/1999 |
| FR | 2 797 877 | 3/2001 |
| FR | 2800612 | 5/2001 |
| FR | 2811993 | 1/2002 |
| FR | 2820032 | 8/2002 |
| FR | 2830189 | 4/2003 |
| GB | 746864 | 3/1956 |
| GB | 759385 | 10/1956 |
| GB | 1214394 | 1/1970 |
| GB | 1546809 | 5/1979 |
| GB | 1554331 | 10/1979 |
| JP | 48-17362 | 5/1973 |
| JP | 54-86521 | 7/1979 |
| JP | 2-200612 | 8/1990 |
| JP | 6-128128 | 5/1994 |
| JP | 6-183935 | 7/1994 |
| JP | 6-227954 | 8/1994 |
| JP | 8-183716 | 7/1996 |
| JP | 8-208448 | 8/1996 |
| JP | 8-259426 | 10/1996 |
| JP | 9-183714 | 7/1997 |
| JP | 10-236929 | 9/1998 |
| JP | 11-021214 | 1/1999 |
| JP | 11-60453 | 3/1999 |
| JP | 11-343218 | 12/1999 |
| JP | 2000-01417 | 1/2000 |
| JP | 2000-86472 | 3/2000 |
| JP | 2000-505841 | 5/2000 |
| JP | 2001-172120 | 6/2001 |
| JP | 2001-220330 | 8/2001 |
| JP | 2001-226217 | 8/2001 |
| JP | 2001-261534 | 9/2001 |
| JP | 2001-261536 | 9/2001 |
| JP | 2001-294519 | 10/2001 |
| JP | 2001-302473 | 10/2001 |
| JP | 2001-516701 | 10/2001 |
| JP | 2001-516705 | 10/2001 |
| JP | 2001-516706 | 10/2001 |
| JP | 2001-516707 | 10/2001 |
| JP | 2002-12523 | 1/2002 |
| JP | 2002-12530 | 1/2002 |
| JP | 2002-047151 | 2/2002 |
| JP | 2002-226338 | 8/2002 |
| JP | 2002-249419 | 9/2002 |
| JP | 2002-326911 | 11/2002 |
| JP | 2003-55177 | 2/2003 |
| JP | 2004-059468 | 2/2004 |
| JP | 2004-307494 | 11/2004 |
| JP | 2004-307495 | 11/2004 |
| WO | WO 93/11103 | 6/1993 |
| WO | WO 93/23009 | 11/1993 |
| WO | WO 93/23446 | 11/1993 |
| WO | WO 94/02022 | 2/1994 |
| WO | WO 95/00578 | 1/1995 |
| WO | WO 95/01772 | 1/1995 |
| WO | WO 95/15144 | 6/1995 |
| WO | WO 97/18795 | 5/1997 |
| WO | WO 99/12846 | 3/1999 |
| WO | WO 99/13822 | 3/1999 |
| WO | WO 99/13823 | 3/1999 |
| WO | WO 99/13824 | 3/1999 |
| WO | WO 99/13828 | 3/1999 |
| WO | WO 99/13841 | 3/1999 |
| WO | WO 99/13844 | 3/1999 |
| WO | WO 99/13845 | 3/1999 |
| WO | WO 99/13846 | 3/1999 |
| WO | WO 99/13847 | 3/1999 |
| WO | WO 99/13849 | 3/1999 |
| WO | WO 99/20235 A1 | 4/1999 |
| WO | WO 00/68282 | 11/2000 |
| WO | WO 01/43714 A1 | 6/2001 |
| WO | WO 01/62759 A1 | 8/2001 |
| WO | WO 01/78669 | 10/2001 |
| WO | WO 02/32386 A2 | 4/2002 |
| WO | WO 02/38115 A1 | 5/2002 |
| WO | WO 02/39964 A1 | 5/2002 |
| WO | WO 02/45673 A2 | 6/2002 |
| WO | WO 02/58646 A1 | 8/2002 |
| WO | WO 02/58647 A1 | 8/2002 |
| WO | WO 02/74270 | 9/2002 |
| WO | WO 03/22232 A2 | 3/2003 |
| WO | WO 03/28685 A1 | 4/2003 |
| WO | WO 03/029359 | 4/2003 |

OTHER PUBLICATIONS

Co-pending U.S. Appl. No. 10/742,995, filed Dec. 23, 2003.
Co-pending U.S. Appl. No. 10/814,334, filed Apr. 1, 2004.
Co-pending U.S. Appl. No. 10/814,333, filed Apr. 1, 2004.
Co-pending U.S. Appl. No. 10/814,430, filed Apr. 1, 2004.
Co-pending U.S. Appl. No. 10/814,305, filed Apr. 1, 2004.
Co-pending U.S. Appl. No. 10/814,300, filed Apr. 1, 2004.
Co-pending U.S. Appl. No. 10/814,428, filed Apr. 1, 2004.
Co-pending U.S. Appl. No. 10/490,869, filed Apr. 1, 2004.
Co-pending U.S. Appl. No. 10/814,236, filed Apr. 1, 2004.
Co-pending U.S. Appl. No. 10/814,338, filed Apr. 1, 2004.
Co-pending U.S. Appl. No. 10/814,335, filed Apr. 1, 2004.
Co-pending U.S. Appl. No. 10/814,336, filed Apr. 1, 2004.
English language Derwent Abstract for DE 33 13 332.
English Language Derwent Abstract of DE 100 29 441.
English Language Derwent Abstract of DE 101 41 683.
English Language Derwent Abstract of DE 101 48 844.
English Language Derwent Abstract of DE 199 23 438.
English Language Derwent Abstract of DE 199 26 377.
English Language Derwent Abstract of EP 0 080 976.
English Language Derwent Abstract of EP 0 087 060.
English Language Derwent Abstract of EP 1 023 891.
English Language Derwent Abstract of EP 1 099 437.
English Language Derwent Abstract of FR 2 589 476.
English Language Derwent Abstract of FR 2 773,470.
English Language Derwent Abstract of FR 2 797 877.
English Language Derwent Abstract of FR 2,800,612.
English Language Derwent Abstract of JP 2-200612.
English Language Derwent Abstract of JP 6-183935.
English Language Derwent Abstract of JP 6-227954.
English Language Derwent Abstract of JP 8-183716.
English Language Derwent Abstract of JP 8-208448.
English Language Derwent Abstract of JP 9-183714.
English Language Derwent Abstract of JP 10-236929.
English Language Derwent Abstract of JP 11-060453.
English Language Derwent Abstract of JP 11-21214.
English Language Derwent Abstract of JP 2000-1417.
English Language Derwent Abstract of JP 2000-086472.
English Language Derwent Abstract of JP 2001-172120.
English Language Derwent Abstract of JP 2001-22030.
English Language Derwent Abstract of JP 2001-261534.
English Language Derwent Abstract of JP 2001-294519.
English Language Derwent Abstract of JP 2001-302473.
English Language Derwent Abstract of JP 2001-516701.
English Language Derwent Abstract of JP 2001-516705.
English Language Derwent Abstract of JP 2001-516706.
English Language Derwent Abstract of JP 2001-516707.

English Language Derwent Abstract of JP 2002-047151.
English Language Derwent Abstract of JP 2002-226338.
English Language Derwent Abstract of JP 2002-249419.
English Language Derwent Abstract of JP 2002-326911.
English Language Derwent Abstract of JP 2004-59468.
English Language Derwent Abstract of WO 02/32386.
French Search Report for French Patent Application No. FR 02/16669, priority document for U.S. Appl. No. 10/742,995, Aug. 6, 2003.
French Search Report for French Patent Application No. FR 03/04021, priority document for U.S. Appl. No. 10/814,337, Dec. 8, 2003.
French Search Report for French Patent Application No. FR 03/04022, priority document for co-pending U.S. Appl. No. 10/814,336, Nov. 20, 2003.
French Search Report for French Patent Application No. FR 03/04024, priority document for co-pending U.S. Appl. No. 10/814,585, Dec. 8, 2003.
French Search Report for French Patent Application No. FR 03/04026, priority document for co-pending U.S. Appl. No. 10/814,335, Nov. 21, 2003.
French Search Report for French Patent Application No. FR 03/04027, priority document for co-pending U.S. Appl. No. 10/814,428, Nov. 28, 2003.
French Search Report for French Patent Application No. FR 03/04028, priority document for co-pending U.S. Appl. No. 10/814,236, Nov. 25, 2003.
French Search Report for French Patent Application No. FR 03/04029, priority document for co-pending U.S. Appl. No. 10/814,430, Feb. 5, 2004.
French Search Report for French Patent Application No. FR 03/04030, priority document for co-pending U.S. Appl. No. 10/814,300, Nov. 27, 2003.
French Search Report for French Patent Application No. FR 03/04031, priority document for co-pending U.S. Appl. No. 10/814,333, Jan. 8, 2004.
French Search Report for French Patent Application No. FR 03/04033, priority document for co-pending U.S. Appl. No. 10/814,334, Nov. 28, 2003.
French Search Report for French Patent Application No. FR 03/04034, priority document for co-pending U.S. Appl. No. 10/814,338, Feb. 17, 2004.
French Search Report for French Patent Application No. FR 03/04035, priority document for co-pending U.S. Appl. No. 10/814,305, Feb. 5, 2004.
International Search Report for PCT Application No. PCT/FR 02/03252, (for co-pending U.S. Appl. No. 10/490,869), Jan. 20, 2003.
Office Action mailed Nov. 2, 2005 in co-pending U.S. Appl. No. 10/742,995.
Office Action mailed Apr. 6, 2006 in co-pending U.S. Appl. No. 10/742,995.
Office Action mailed Mar. 27, 2006 in co-pending U.S. Appl. No. 10/814,334.
Office Action mailed May 18, 2006 in co-pending U.S. Appl. No. 10/814,333.
Office Action mailed Jun. 8, 2006 in co-pending U.S. Appl. No. 10/814,430.
Office Action mailed Mar. 15, 2006 in co-pending U.S. Appl. No. 10/814,305.
Office Action mailed Aug. 24, 2006 in co-pending U.S. Appl. No. 10/814,305.
Office Action mailed Mar. 23, 2006 in co-pending U.S. Appl. No. 10/814,300.
Office Action mailed Aug. 28, 2006 in co-pending U.S. Appl. No. 10/814,300.
Office Action mailed Nov. 2, 2005 in co-pending U.S. Appl. No. 10/814,338.
Office Action mailed May 30, 2006 in co-pending U.S. Appl. No. 10/814,338.
Office Action mailed Nov. 3, 2005 in co-pending U.S. Appl. No. 10/490,869.
Office Action mailed May 26, 2006 in co-pending U.S. Appl. No. 10/490,869.
Office Action mailed Mar. 24, 2006 in co-pending U.S. Appl. No. 10/814,236.
Office Action mailed Aug. 28, 2006 in co-pending U.S. Appl. No. 10/814,236.
Office Action mailed May 25, 2006 in co-pending U.S. Appl. No. 10/814,335.
Office Action mailed Nov. 17, 2005 in co-pending U.S. Appl. No. 10/814,336.
Office Action mailed Jun. 21, 2006 in co-pending U.S. Appl. No. 10/814,336.
Jacobi, Otto and Jacobi, Gertrud, "Investigation into the reciprocal action of cosmetics and the biosphere of the stratum corneuum of the skin," *Cosmetics and Toiletries*, 91:25-32 (Jan. 1976).
Science Des Traitements Capillaires [Hair Treatment Sciences] by Charles Zviak, 1988, published by Masson, pp. 215 and 278.
M. Schlossmann, "The Chemistry and Manufacture of Cosmetics Formulating," 2(3):522-526 (2000).
D.F. Williams et al., "Chemistry and Technology of the Cosmetics and Toiletries Industry," ed. 2, pp. 77-78 (1996).
Yuuki Kagoubutsu Jilen (Dictionary of Organic Compounds), Kodansha Ltd., Aug. 10, 2002, p. 908.
G. Fonnum, J. Bakke and Fk. Hansen—Colloid Polym. Sci 271, 380-389 (1993).
Zviak, C., The Science of Hair Care, pp. 215 and 278 (1986).
Mishra, J.K. et al. Synthesis of some bischromophoric dyes containing nonabsorbing flexible bridge, Indian Journal of Chemistry, vol. 31B, pp. 118-122, Feb. 1992.

* cited by examiner

COMPOSITION FOR DYEING HUMAN KERATIN MATERIALS, COMPRISING A FLUORESCENT DYE AND A PARTICULAR SEQUESTERING AGENT, PROCESS THEREFOR AND USE THEREOF

The invention relates to a composition comprising at least one fluorescent dye and at least one particular sequestering agent, and also to processes and a device for using these compositions. The present invention similarly relates to the use of a composition comprising at least one fluorescent dye and at least one particular sequestering agent, to dye with a lightening effect human keratin materials and more particularly keratin fibres such as artificially dyed or pigmented hair, and also coloured skin.

It is common for individuals with coloured skin to wish to lighten their skin and for this purpose to use cosmetic or dermatological compositions containing bleaching agents.

The substances most commonly used as bleaching agent are hydroquinone and its derivatives, kojic acid and its derivatives, azelaic acid, arbutin and its derivatives, alone or in combination with other active agents.

However, these agents are not without their drawbacks. In particular, they need to be used for a long time and in large amounts in order to obtain a bleaching effect on the skin. No immediate effect is observed on applying compositions comprising them.

In addition, hydroquinone and its derivatives are used in an amount that is effective to produce a visible bleaching effect. In particular, hydroquinone is known for its cytotoxicity towards melanocytes.

Moreover, kojic acid and its derivatives have the drawback of being expensive and consequently of not being able to be used in large amount in products for commercial mass distribution.

There is thus still a need for cosmetic compositions that allow a lighter, uniform, homogeneous tone of natural appearance to be obtained, these compositions having satisfactory transparency after application to the skin.

In the field of haircare, there are mainly two major types of hair dyeing.

The first is semi-permanent dyeing or direct dyeing, which uses dyes capable of giving the hair's natural colour a more or less pronounced modification that withstands shampooing several times. These dyes are known as direct dyes and may be used in two different ways. The dyeing may be performed by applying the composition containing the direct dye(s) directly to the keratin fibres, or by applying a mixture, prepared extemporaneously, of a composition containing the direct dye(s) with a composition containing an oxidizing bleaching agent, which is preferably aqueous hydrogen peroxide solution. Such a process is then termed "lightening direct dyeing".

The second is permanent dyeing or oxidation dyeing. This is performed with "oxidation" dye precursors, which are colourless or weakly coloured compounds which, once mixed with oxidizing products, at the time of use, can give rise to coloured compounds and dyes via a process of oxidative condensation. It is often necessary to combine one or more direct dyes with the oxidation bases and couplers in order to neutralize or attenuate the shades with too much of a red, orange or golden glint or, on the contrary, to accentuate these red, orange or golden glints.

Among the available direct dyes, nitrobenzene direct dyes are not sufficiently strong, and indo-amines, quinone dyes and natural dyes have low affinity for keratin fibres and consequently lead to dyeing that is not sufficiently fast with respect to the various treatments to which the fibres may be subjected, and in particular with respect to shampooing.

In addition, there is a need to obtain a lightening effect on human keratin fibres. This lightening is conventionally obtained via a process of bleaching the melanins of the hair via an oxidizing system generally consisting of hydrogen peroxide optionally combined with persalts. This bleaching system has the drawback of degrading the keratin fibres and of impairing their cosmetic properties.

The object of the present invention is to solve the problems mentioned above and especially to propose a composition that has good dyeing affinity for keratin materials and especially keratin fibres, good resistance properties with respect to external agents, and in particular with respect to shampooing, and that also makes it possible to obtain lightening without impairing the treated material, more particularly the keratin fibre.

It has thus been found, surprisingly and unexpectedly, that the use of fluorescent dyes, in particular those in the orange range, in the presence of particular sequestering agents, allows these objectives to be achieved.

A first subject of the present invention is thus a composition comprising, in a cosmetically acceptable medium, at least one fluorescent dye that is soluble in the said medium and at least one complexing agent chosen from hydroxycarboxylic acids and polycarboxylic acids, and the monovalent or divalent alkali metal, alkaline-earth metal, transition metal, organic amine or ammonium salts thereof, alone or as mixtures; the composition not comprising, as fluorescent agent, 2-[2-(4-dialkylamino)phenylethenyl]-1-alkylpyridinium in which the alkyl radical of the pyridinium nucleus represents a methyl or ethyl radical and that of the benzene nucleus represents a methyl radical, and in which the counterion is a halide.

A second subject of the invention concerns a process for dyeing human keratin fibres with a lightening effect, in which the following steps are performed:

a) a composition according to the invention is applied to the said fibres, for a time that is sufficient to develop the desired coloration and lightening, b) the fibres are optionally rinsed, c) the fibres are optionally washed with shampoo and rinsed, d) the fibres are dried or are left to dry.

Another subject of the invention concerns the use of a composition comprising, in a cosmetically acceptable medium, at least one fluorescent dye that is soluble in the said medium and at least one complexing agent chosen from hydroxycarboxylic acids and polycarboxylic acids, and the monovalent or divalent alkali metal, alkaline-earth metal, transition metal, organic amine or ammonium salts thereof, alone or as mixtures, to dye with a lightening effect human keratin materials.

A multi-compartment device for dyeing and lightening keratin fibres, comprising at least one compartment containing the composition according to the invention, and at least one other compartment containing a composition containing at least one oxidizing agent, constitutes a final subject of the invention.

The compositions of the invention in particular allow an increased fluorescent effect and a lightening effect that is greater than that obtained with the fluorescent dye used alone.

Better resistance of the result with respect to washing or shampooing is also found.

However, other characteristics and advantages of the present invention will emerge more clearly on reading the description and the examples that follow.

Unless otherwise indicated, the limits of the ranges of values that are given in the description are included within these ranges.

As has been mentioned previously, the composition according to the invention comprises at least one fluorescent dye and at least one particular sequestering agent.

For the purposes of the present invention, the term "fluorescent dye" means a dye which is a molecule that colours by itself, and thus absorbs light in the visible spectrum and possibly in the ultraviolet spectrum (wavelengths ranging from 360 to 760 nanometers), but which, in contrast with a standard dye, converts the absorbed energy into fluorescent light of longer wavelength emitted in the visible region of the spectrum.

A fluorescent dye according to the invention is to be differentiated from an optical brightener. Optical brighteners, which are also known as brighteners, fluorescent brighteners, fluorescent brightening agents, fluorescent whitening agents, whiteners or fluorescent whiteners, are colourless transparent compounds, which do not dye because they do not absorb light in the visible region, but only in the ultraviolet region (wavelengths ranging from 200 to 400 nanometers), and convert the absorbed energy into fluorescent light of longer wavelength emitted in the visible region of the spectrum; the colour impression is then generated solely by purely fluorescent light that is predominantly blue (wavelengths ranging from 400 to 500 nanometers).

Finally, the fluorescent dye used in the composition is soluble in the medium of the composition. It should be pointed out that the fluorescent dye differs therein from a fluorescent pigment, which itself is insoluble in the medium of the composition.

More particularly, the fluorescent dye used in the context of the present invention, which is optionally neutralized, is soluble in the medium of the composition to at least 0.001 g/l, more particularly at least 0.5 g/l, preferably at least 1 g/l and, according to one even more preferred embodiment, at least 5 g/l at a temperature of between 15 and 25° C.

Moreover, according to one characteristic of the invention, the composition does not comprise, as fluorescent dye, a 2-[2-(4-dialkylamino)phenylethenyl]-1-alkylpyridinium in which the alkyl radical of the pyridinium nucleus represents a methyl or ethyl radical and that of the benzene nucleus represents a methyl radical, and in which the counterion is a halide.

In accordance with an even more particular embodiment of the invention, the composition does not comprise, as fluorescent dye, a compound chosen from azo, azomethine or methine monocationic heterocyclic fluorescent dyes.

The fluorescent dyes preferably used according to the present invention are dyes in the orange range.

Preferably, the fluorescent dyes of the invention lead to a reflectance maximum that is in the wavelength range from 500 to 650 nanometers and preferably in the wavelength range from 550 to 620 nanometers.

Some of the fluorescent dyes according to the present invention are compounds that are known per se.

As examples of fluorescent dyes that may be used, mention may be made of the fluorescent dyes belonging to the following families: naphthalimides; cationic or non-cationic coumarins; xanthenodiquinolizines (such as, especially, sulphorhodamines); azaxanthenes; naphtholactams; azlactones; oxazines; thiazines; dioxazines; polycationic fluorescent dyes of azo, azomethine or methine type, alone or as mixtures, and preferably belonging to the following families: naphthalimides; cationic or non-cationic coumarins; azaxanthenes; naphtholactams; azlactones; oxazines; thiazines; dioxazines; polycationic fluorescent dyes of azo, azomethine or methine type, alone or as mixtures.

More particularly, the following may be mentioned among the above dyes:

Brilliant Yellow B6GL sold by the company Sandoz and having the following structure:

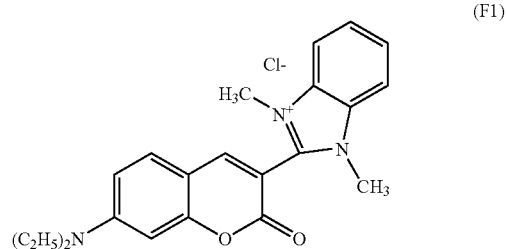

(F1)

Basic Yellow 2, or Auramine O, sold by the companies Prolabo, Aldrich or Carlo Erba and having the following structure:

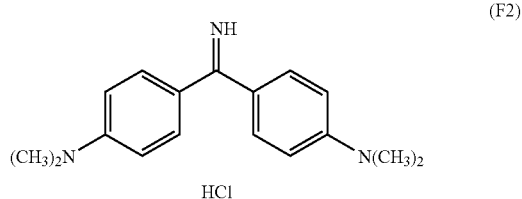

(F2)

4,4'-(imidocarbonyl)bis(N,N-dimethylaniline) monohydrochloride—CAS number 2465-27-2.

Mention may also be made of the compounds having the following formula:

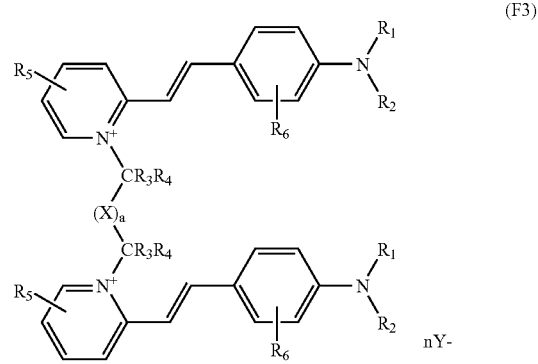

(F3)

in which:
$R_1$ and $R_2$, which may be identical or different, represent:
  a hydrogen atom;
  a linear or branched alkyl radical containing 1 to 10 carbon atoms and preferably from 1 to 4 carbon atoms, optionally interrupted and/or substituted with at least one hetero atom and/or group containing at least one hetero atom and/or substituted with at least one halogen atom;

an aryl or arylalkyl radical, the aryl group containing 6 carbon atoms and the alkyl radical containing 1 to 4 carbon atoms; the aryl radical optionally being substituted with one or more linear or branched alkyl radicals containing 1 to 4 carbon atoms optionally interrupted and/or substituted with at least one hetero atom and/or group containing at least one hetero atom and/or substituted with at least one halogen atom;

$R_1$ and $R_2$ may optionally be linked so as to form a heterocycle with the nitrogen atom and may contain one or more other hetero atoms, the heterocycle optionally being substituted with at least one linear or branched alkyl radical preferably containing from 1 to 4 carbon atoms and optionally being interrupted and/or substituted with at least one hetero atom and/or group containing at least one hetero atom and/or substituted with at least one halogen atom;

$R_1$ or $R_2$ may optionally be engaged in a heterocycle containing the nitrogen atom and one of the carbon atoms of the phenyl group bearing the said nitrogen atom;

$R_3$ and $R_4$, which may be identical or different, represent a hydrogen atom or an alkyl radical containing 1 to 4 carbon atoms;

$R_5$, which may be identical or different, represent a hydrogen atom, a halogen atom or a linear or branched alkyl radical containing 1 to 4 carbon atoms, optionally interrupted with at least one hetero atom;

$R_6$, which may be identical or different, represent a hydrogen atom; a halogen atom; a linear or branched alkyl radical containing 1 to 4 carbon atoms, optionally substituted and/or interrupted with at least one hetero atom and/or group bearing at least one hetero atom and/or substituted with at least one halogen atom;

X represents:
  a linear or branched alkyl radical containing 1 to 14 carbon atoms or an alkenyl radical containing 2 to 14 carbon atoms, optionally interrupted and/or substituted with at least one hetero atom and/or group containing at least one hetero atom and/or substituted with at least one halogen atom;
  a 5- or 6-membered heterocyclic radical optionally substituted with at least one linear or branched alkyl radical containing 1 to 14 carbon atoms, optionally substituted with at least one hetero atom; with at least one linear or branched aminoalkyl radical containing 1 to 4 carbon atoms, optionally substituted with at least one hetero atom; with at least one halogen atom;
  a fused or non-fused aromatic or diaromatic radical, optionally separated by an alkyl radical containing 1 to 4 carbon atoms, the aryl radical(s) optionally being substituted with at least one halogen atom or with at least one alkyl radical containing 1 to 10 carbon atoms optionally substituted and/or interrupted with at least one hetero atom and/or group bearing at least one hetero atom;
  a dicarbonyl radical;
  the group X possibly bearing one or more cationic charges;

a being equal to 0 or 1;

$Y^-$, which may be identical or different, representing an organic or inorganic anion;

n being an integer at least equal to 2 and at most equal to the number of cationic charges present in the fluorescent compound.

It should be recalled that the term "hetero atom" represents an oxygen or nitrogen atom.

Among the groups bearing such atoms that may be mentioned, inter alia, are hydroxyl, alkoxy, carbonyl, amino, ammonium, amido (—N—CO—) and carboxyl (—O—CO— or —CO—O—) groups.

As regards the alkenyl groups, they contain one or more unsaturated carbon-carbon bonds (—C=C—) and preferably only one carbon-carbon double bond.

In this general formula, the radicals $R_1$ and $R_2$, which may be identical or different, more particularly represent:
  a hydrogen atom;
  an alkyl radical containing 1 to 10 carbon atoms, especially 1 to 6 carbon atoms and preferably 1 to 4 carbon atoms, optionally interrupted with an oxygen atom or optionally substituted with at least one hydroxyl, amino or ammonium radical or a chlorine or fluorine atom;
  a benzyl or phenyl radical optionally substituted with an alkyl or alkoxy radical containing 1 to 4 carbon atoms and preferably 1 or 2 carbon atoms;
  with the nitrogen atom, a heterocyclic radical of the pyrrolo, pyrrolidino, imidazolino, imidazolo, imidazolium, pyrazolino, piperazino, morpholino, morpholo, pyrazolo or triazolo type, optionally substituted with at least one linear or branched alkyl radical containing 1 to 4 carbon atoms optionally interrupted and/or substituted with a nitrogen and/or oxygen atom and/or group bearing a nitrogen and/or oxygen atom.

As regards the abovementioned amino or ammonium radicals, the radicals borne by the nitrogen atom may be identical or different and may more particularly represent a hydrogen atom, a $C_1$–$C_{10}$ and preferably $C_1$–$C_4$ alkyl radical or an arylalkyl radical in which, more especially, the aryl radical contains 6 carbon atoms and the alkyl radical contains 1 to 10 carbon atoms and preferably 1 to 4 carbon atoms.

According to one advantageous embodiment of the invention, the radicals $R_1$ and $R_2$, which may be identical or different, represent a hydrogen atom; a linear or branched $C_1$–$C_6$ alkyl radical; a $C_2$–$C_6$ alkyl radical substituted with a hydroxyl radical; a $C_2$–$C_6$ alkyl radical bearing an amino or ammonium group; a $C_2$–$C_6$ chloroalkyl radical; a $C_2$–$C_6$ alkyl radical interrupted with an oxygen atom or a group bearing an oxygen atom (for example ester); an aromatic radical, for instance phenyl, benzyl or 4-methylphenyl; a heterocyclic radical such as pyrrolo, pyrrolidino, imidazolo, imidazolino, imidazolium, piperazino, morpholo, morpholino, pyrazolo or triazolo radicals, optionally substituted with at least one $C_1$–$C_6$ alkyl or aromatic radical.

Preferably, the radicals $R_1$ and $R_2$, which may be identical or different, represent a hydrogen atom, a linear or branched $C_1$–$C_6$ alkyl radical such as methyl, ethyl, n-butyl or n-propyl radicals; 2-hydroxyethyl; an alkyltrimethylammonium or alkyltriethylammonium radical, the alkyl radical being a linear $C_2$–$C_6$ alkyl radical; a (di)alkylmethylamino or (di)alkylethylamino radical, the alkyl radical being a linear $C_1$–$C_6$ alkyl radical; —CH$_2$CH$_2$Cl; —(CH$_2$)$_n$—OCH$_3$ or —(CH$_2$)$_n$—OCH$_2$CH$_3$ with n being an integer ranging from 2 to 6; —CH$_2$CH$_2$—OCOCH$_3$; —CH$_2$CH$_2$COOCH$_3$.

Preferably, the radicals $R_1$ and $R_2$, which may be identical or different, and which are preferably identical, represent a methyl radical or an ethyl radical.

The radicals $R_1$ and $R_2$, which may be identical or different, may also represent a heterocyclic radical of the pyrrolidino, 3-aminopyrrolidino, 3-(dimethyl)-aminopyrrolidino, 3-(trimethyl)aminopyrrolidino, 2,5-dimethylpyrrolo, 1H-imidazolo, 4-methylpiperazino, 4-benzylpiperazino, morpholo, 3,5-(tert-butyl)-1H-pyrazolo, 1H-pyrazolo or 1H-1,2,4-triazolo type.

The radicals $R_1$ and $R_2$, which may be identical or different, may also represent radicals linked so as to form a heterocycle of formulae (I) and (II) below:

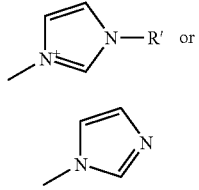

in which R' represents a hydrogen atom or a $C_1$–$C_3$ alkyl radical, —$CH_2CH_2OH$, —$CH_2CH_2OCH_3$.

In accordance with a more particular embodiment of the invention, $R_5$, which may be identical or different, represent a hydrogen atom, a fluorine or chlorine atom or a linear or branched alkyl radical containing 1 to 4 carbon atoms optionally interrupted with an oxygen or nitrogen atom.

It is pointed out that the substituent $R_5$, if it is other than hydrogen, is advantageously in position(s) 3 and/or 5 relative to the carbon of the ring bearing the nitrogen substituted with the radicals $R_1$ and $R_2$, and preferably in position 3 relative to that carbon.

Advantageously, the radicals $R_5$, which may be identical or different, represent a hydrogen atom; a linear or branched $C_1$–$C_4$ alkyl radical; —O—$R_{51}$ with $R_{51}$ representing a linear $C_1$–$C_4$ alkyl radical; —$R_{52}$—O—$CH_3$ with $R_{52}$ representing a linear $C_2$–$C_3$ alkyl radical; —$R_{53}$—N $(R_{54})_2$ in which $R_{53}$ represents a linear $C_2$–$C_3$ alkyl radical and $R_{54}$, which may be identical or different, represent a hydrogen atom or a methyl radical.

Preferably, $R_5$, which may be identical or different, represent hydrogen, a methyl or a methoxy, and $R_5$ preferentially represents a hydrogen atom.

According to one particular embodiment, the radicals $R_6$, which may be identical or different, represent a hydrogen atom; a linear or branched $C_1$–$C_4$ alkyl radical; —X with X representing a chlorine, bromine or fluorine atom; —$R_{61}$—O—$R_{62}$ with $R_{61}$ representing a linear $C_2$–$C_3$ alkyl radical and $R_{62}$ representing a methyl radical; —$R_{63}$—$N(R_{64})_2$ with $R_{63}$ representing a linear $C_2$–$C_3$ alkyl radical and $R_{64}$, which may be identical or different, representing a hydrogen atom or a methyl radical; —$N(R_{65})_2$ in which $R_{65}$, which may be identical or different, represent a hydrogen atom or a linear $C_2$–$C_3$ alkyl radical; —$NHCOR_{66}$ with $R_{66}$ representing a $C_1$–$C_2$ alkyl radical, a $C_1$–$C_2$ chloroalkyl radical, a radical —$R_{67}$—$NH_2$ or —$R_{67}$—$NH(CH_3)$ or —$R_{67}$—$N(CH_3)_2$ or —$R_{67}$—$N^+(CH_3)_3$ or —$R_{67}$—$N^+(CH_2CH_3)_3$ with $R_{67}$ representing a $C_1$–$C_2$ alkyl radical.

It is pointed out that the substituent $R_6$, if it is other than hydrogen, is preferably in position 2 and/or 4 relative to the nitrogen atom of the pyridinium ring, and preferentially in position 4 relative to that nitrogen atom.

More particularly, these radicals $R_6$, which may be identical or different, represent a hydrogen atom or a methyl or ethyl radical, and $R_6$ preferably represents a hydrogen atom.

As regards the radicals $R_3$ and $R_4$, these radicals, which may be identical or different, advantageously represent a hydrogen atom or an alkyl radical containing 1 to 4 carbon atoms and more especially a methyl radical. Preferably, $R_3$ and $R_4$ each represent a hydrogen atom.

As mentioned above, X represents:

a linear or branched alkyl radical containing 1 to 14 carbon atoms or an alkenyl radical containing 2 to 14 carbon atoms, optionally interrupted and/or substituted with at least one hetero atom, with at least one group bearing at least one hetero atom and/or with at least one halogen atom;

a 5- or 6-membered heterocyclic radical optionally substituted with at least one linear or branched alkyl radical containing 1 to 14 carbon atoms, with at least one linear or branched aminoalkyl radical containing 1 to 4 carbon atoms, optionally substituted with at least one hetero atom; with at least one halogen atom;

a fused or non-fused aromatic or diaromatic radical, optionally separated by an alkyl radical containing 1 to 4 carbon atoms, the aryl radical(s) optionally being substituted with at least one halogen atom or with at least one alkyl radical containing 1 to 10 carbon atoms optionally substituted and/or interrupted with at least one hetero atom and/or group bearing at least one hetero atom;

a dicarbonyl radical.

In addition, it is indicated that the group X may bear one or more cationic charges.

Thus, X may represent a linear or branched alkyl radical containing 1 to 14 carbon atoms or an alkenyl radical containing 2 to 14 carbon atoms, and may be substituted and/or interrupted with one or more oxygen and/or nitrogen atoms, and/or with one or more groups bearing at least one hetero atom, and/or with a fluorine or chlorine atom.

Among the groups of this type that may be mentioned most particularly are hydroxyl, alkoxy (especially with a radical R of the $C_1$–$C_4$ alkyl type), amino, ammonium, amido, carbonyl and carboxyl groups (—COO— or —O—CO—) especially with a radical of alkyloxy type.

It should be noted that the nitrogen atom, if it is present, may be in a quaternized or non-quaternized form. In this case, the other radical or the other two radicals borne by the quaternized or non-quaternized nitrogen atom is (are) identical or different and may be a hydrogen atom or a $C_1$–$C_4$ alkyl radical, preferably methyl.

According to another variant, the group X represents a 5- or 6-membered heterocyclic radical of the imidazolo, pyrazolo, triazino or pyridino type, optionally substituted with at least one linear or branched alkyl radical containing 1 to 14 carbon atoms, more particularly 1 to 10 carbon atoms and preferably from 1 to 4 carbon atoms; with at least one linear or branched aminoalkyl radical containing 1 to 10 carbon atoms and preferably from 1 to 4 carbon atoms, optionally substituted with a group containing at least one hetero atom (preferably a hydroxyl radical), or with a halogen atom. It should be noted that the amino group is preferably linked to the heterocycle.

In accordance with another possibility, the group X represents an aromatic radical (preferably containing 6 carbon atoms) or fused or non-fused diaromatic radical (especially containing from 10 to 12 carbon atoms), possibly separated by an alkyl radical containing 1 to 4 carbon atoms, the aryl radical(s) optionally being substituted with at least one halogen atom and/or with at least one alkyl radical containing 1 to 10 carbon atoms and preferably 1 to 4 carbon atoms, optionally interrupted with at least one oxygen and/or nitrogen atom and/or a group containing at least one hetero atom (for instance a carbonyl, carboxyl, amido, amino or ammonium radical).

It should be noted that the aromatic radical, preferably a phenyl radical, is linked to the groups $CR_3R_4$ via bonds in positions 1,2; 1,3 or 1,4 and preferably in positions 1,3 and 1,4. If the phenyl radical linked via bonds in positions 1,4 bears one or two substituents, this or these substituent(s) is (are) preferably located in position 1,4 relative to one of the groups $CR_3R_4$. If the phenyl radical linked via bonds in positions 1,3 bears one or two substituent(s), this or these substituent(s) is (are) preferably located in position 1 or 3 relative to one of the groups $CR_3R_4$.

In the case where the radical is diaromatic, it is preferably non-fused and comprises two phenyl radicals possibly separated by a single bond (i.e. a carbon of each of the two rings) or by an alkyl radical, preferably of $CH_2$ or $C(CH_3)_2$ type. Preferably, the aromatic radicals do not bear a substituent. It should be noted that the said diaromatic radical is linked to the groups $CR_3R_4$ via bonds in positions 4,4'.

As examples of groups X that are suitable, mention may be made especially of linear or branched alkyl radicals containing 1 to 13 carbon atoms, such as methylene, ethylene, propylene, isopropylene, n-butylene, pentylene and hexylene; 2-hydroxypropylene and 2-hydroxy-n-butylene; $C_1$–$C_{13}$ alkylene radicals substituted or interrupted with one or more nitrogen and/or oxygen atoms, and/or groups bearing at least one hetero atom (hydroxyl, amino, ammonium, carbonyl or carboxyl, for example), such as —$CH_2CH_2OCH_2CH_2$—, 1,6-dideoxy-d-mannitol, —$CH_2N^+(CH_3)_2CH_2$—, —$CH_2CH_2N^+(CH_3)_2$—$(CH_2)_6N^+$ $(CH_3)_2$—$CH_2CH_2$—, CO—CO—, 3,3-di-methylpentylene, 2-acetoxyethylene, butylene-1,2,3,4-tetraol; —CH=CH—; aromatic or diaromatic radicals substituted with one or more alkyl radicals, with one or more groups bearing at least one hetero atom and/or with one or more halogen atoms, such as 1,4-phenylene, 1,3-phenylene, 1,2-phenylene, 2,6-fluorobenzene, 4,4'-biphenylene, 1,3-(5-methylbenzene), 1,2-bis (2-methoxy)benzene, bis(4-phenyl)methane, methyl 3,4-benzoate and 1,4-bis(amidomethyl)phenyl; radicals of heterocyclic type, for instance pyridine or a derivative thereof such as 2,6-bispyridine, imidazole, imidazolium or triazine.

According to a more particular embodiment of the invention, X represents a linear or branched $C_1$–$C_{13}$ alkyl radical; —$CH_2CH(OH)CH_2$—; —$CH_2CH(Cl)CH_2$—; —$CH_2CH_2$—$OCOCH_2$—; —$CH_2CH_2COOCH_2$—; —Ra—O—Rb— with Ra representing a linear $C_2$–$C_6$ alkyl radical and Rb representing a linear $C_1$–$C_2$ alkyl radical; —Rc—N (Rd)—Re— with Rc representing a $C_2$–$C_9$ alkyl radical, Rd representing a hydrogen atom or a $C_1$–$C_2$ alkyl radical and Re representing a $C_1$–$C_6$ alkyl radical; —Rf—$N^+(Rg)_2$—Rh— with Rf representing a linear $C_2$–$C_9$ alkyl

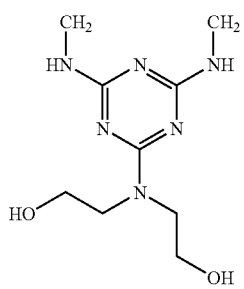

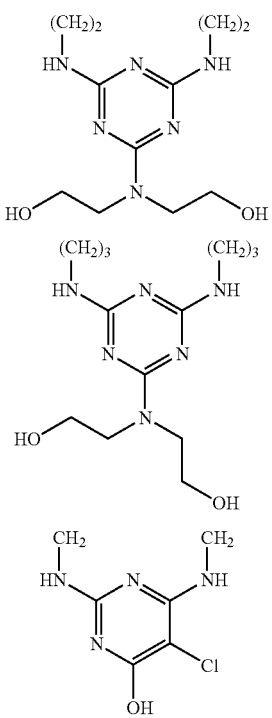

According to another possibility, X may represent the divalent aromatic radicals below:

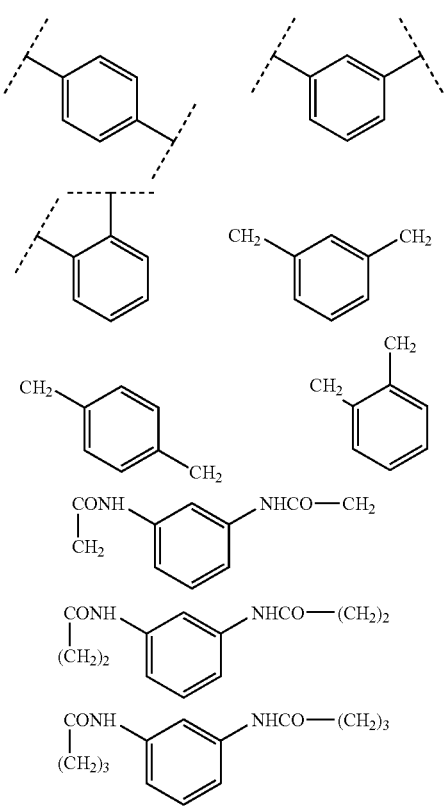

-continued

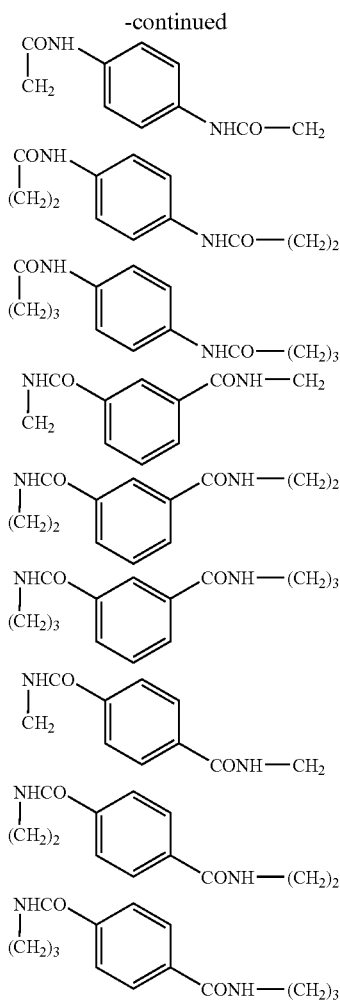

In the general formula of these fluorescent compounds, Y⁻ represents an organic or inorganic anion. If there are several anions Y⁻, these anions may be identical or different.

Among the anions of mineral origin that may be mentioned, without wishing to be limited thereto, are anions derived from halogen atoms, such as chlorides, preferably, or iodides, sulphates or bisulphates, nitrates, phosphates, hydrogen phosphates, dihydrogen phosphates, carbonates and bicarbonates.

Among the anions of organic origin that may be mentioned are anions derived from the salts of saturated or unsaturated, aromatic or non-aromatic monocarboxylic or polycarboxylic, sulphonic or sulphuric acids, optionally substituted with at least one hydroxyl or amino radical, or halogen atoms. Non-limiting examples that are suitable for use include acetates, hydroxyacetates, aminoacetates, (tri) chloroacetates, benzoxyacetates, propionates and derivatives bearing a chlorine atom, fumarates, oxalates, acrylates, malonates, succinates, lactates, tartrates, glycolates, citrates, benzoates and derivatives bearing a methyl or amino radical, alkyl sulphates, tosylates, benzenesulphonates, toluenesulphonates, etc.

Preferably, the anion(s) Y, which may be identical or different, is(are) chosen from chloride, sulphate, methosulphate and ethosulphate.

Finally, the integer n is at least equal to 2 and at most equal to the number of cationic charges present in the fluorescent compound.

Preferably, the fluorescent compounds that have just been described in detail are symmetrical compounds.

These compounds may be synthesized by reacting, in a first step, α-picoline with a reagent containing two leaving groups that may be chosen from halogen atoms, preferably bromine, or optionally chlorine, or groups of tolylsulphonyl or methyl-sulphonyl type.

This first step may take place in the presence of a solvent, although this is not obligatory, for instance dimethylformamide.

The number of moles of α-picoline is generally in the region of 2 per mole of reagent containing the leaving groups.

In addition, the reaction is usually performed at the reflux temperature of the reagent and/or of the solvent if a solvent is present.

The product derived from this first step is then placed in contact with a corresponding aldehyde having the following formula:

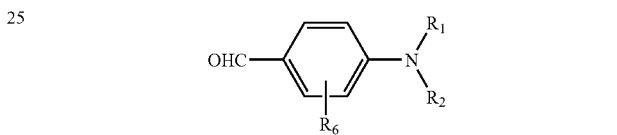

in which $R_1$, $R_2$ and $R_6$ have the same meanings as indicated above.

In this case also, the reaction may be performed in the presence of a suitable solvent, preferably at reflux.

It should be noted that the radicals $R_1$ and $R_2$ of the aldehyde may have the meaning indicated in the general formula detailed previously.

It is also possible to use an aldehyde for which the said radicals represent hydrogen atoms and to perform, in accordance with standard methods, the substitution of these hydrogen atoms with suitable radicals as described in the general formula once the second step is complete.

Reference may be made especially to syntheses as described in U.S. Pat. No. 4,256,458.

The fluorescent dye(s) present in the composition according to the invention advantageously represent(s) from 0.01% to 20% by weight, more particularly from 0.05% to 10% by weight and preferably from 0.1% to 5% by weight, relative to the total weight of the composition.

As mentioned previously, the composition also comprises at least one complexing agent chosen from hydroxycarboxylic acids, polycarboxylic acids and the alkali metal, alkaline-earth metal, transition metal, organic amine or ammonium salts thereof, alone or as mixtures.

Examples of monovalent cations that may be mentioned include cations of alkali metals such as sodium or potassium.

Mention may also be made of monovalent cations derived from organic amines, such as primary, secondary or tertiary amines, or from alkanolamines. The said amines contain one or more radicals, which may be identical or different, of linear or branched C1–C20 alkyl type, optionally containing a hetero atom, for instance oxygen. The cations derived from quaternary ammonium, more particularly containing four radicals, which may be identical or different, corresponding to the definition given above, are also suitable.

Examples of divalent cations that may be mentioned include divalent cations of alkaline-earth metals such as calcium or magnesium, or of transition metals (metals comprising an incomplete d subshell), more particularly in oxidation state II, for instance the divalent cobalt, iron, manganese, zinc or copper cation.

More particularly, the sequestering agents of hydroxycarboxylic type correspond to the following formula (A): R—(CHOH)$_4$—CO$_2$X, in which R represents a CH$_2$OH or CO$_2$X group and X represents a hydrogen or a monovalent or divalent cation. This formula includes all the enantiomers and all the diastereoisomers of these compounds.

As regards the sequestering agents of polycarboxylic type, they more particularly correspond to compounds of the following formula (B):
R—N(Y)(CH(R')CO$_2$X), in which Y represents a hydrogen atom or a group CH(R')CO$_2$X; R represents a hydrogen atom or a group (a) —CH(CO$_2$X)—(CH$_2$)$_n$CO$_2$X, (b) —(CH$_2$)$_n$OH, (c) —CH(R'')CO$_2$X, (d) —(CH$_2$)$_n$N(COR'')—CH$_2$CO$_2$X, (e) —(CH$_2$)$_n$—N(CH$_2$CO$_2$X)CH$_2$CO$_2$X and (f) —(CH$_2$)$_n$NH—CH(CO$_2$X)CH$_2$CO$_2$X, in which R' represents a hydrogen atom or a group CH$_2$CO$_2$X; R'' represents a linear or branched C$_1$–C$_{30}$ or cyclic C$_3$–C$_{30}$ alkyl group, n is an integer between 1 and 5, and X represents a hydrogen atom or a monovalent or divalent cation as defined in the context of formula (A). According to one particular embodiment, n is equal to 2.

Among the sequestering compounds that may be used, the following are particularly suitable:

Formula (A): gluconic acid, mucic acid (or galactaric acid), glucaric acid, mannaric acid, salts thereof, and mixtures thereof;

Formula (B):
  compounds containing four carboxylic acid or salt functions, when R represents a hydrogen atom and R' represents a group —CH$_2$—CO$_2$X, or when R represents a group —CH(CO$_2$X)—(CH$_2$)$_2$—CO$_2$X and R' represents a hydrogen atom;
  compounds comprising three carboxylic acid or salt functions, when R represents a group —CH(CH$_3$)—CO$_2$X and R' represents a hydrogen atom, or when R represents a group —(CH$_2$)$_2$—N(COR'')—CH$_2$—CO$_2$X and R' represents a hydrogen atom.

Methylglycinediacetic acid, N-lauroylethylenediamine-N,N',N'-triacetic acid, iminodisuccinic acid, N,N-dicarboxymethyl-L-glutamic acid, ethylenediamine-N,N'-disuccinic acid, and their salts and mixtures, are preferred examples of compounds of formula (B).

It should be noted that the term "mixture" means a mixture of several acids, a mixture of several salts of an acid or of salts of several acids together, or alternatively a mixture of an acid and of one or more of its salts.

Preferably, the polycarboxylic acids used are of formula (B) in which R represents a hydrogen atom or a group chosen from groups (a) to (d) and (f).

The content of sequestering agent advantageously represents 0.0001% to 20% by weight relative to the weight of the composition, more particularly between 0.001% and 10% by weight relative to the weight of the composition and preferably between 0.01% and 5% by weight relative to the weight of the composition.

The cosmetically acceptable medium generally consists of water or of a mixture of water and of one or more common organic solvents.

Among the solvents that are suitable for use, mention may be made more particularly of alcohols such as ethyl alcohol, isopropyl alcohol, benzyl alcohol and phenylethyl alcohol, or glycols or glycol ethers, for instance ethylene glycol monomethyl ether, monoethyl ether or monobutyl ether, propylene glycol and ethers thereof, for instance propylene glycol monomethyl ether, butylene glycol, dipropylene glycol and diethylene glycol alkyl ethers, for instance diethylene glycol monoethyl ether or monobutyl ether, or alternatively polyols, for instance glycerol. Polyethylene glycols and polypropylene glycols, and mixtures of all these compounds, may also be used as solvent.

The common solvents described above usually represent, if they are present, from 1% to 40% by weight and more preferably from 5% to 30% by weight relative to the total weight of the composition.

The pH of the composition in accordance with the invention is generally between 3 and 12 approximately and preferably between 5 and 11 approximately.

It may be adjusted to the desired value by means of acidifying or basifying agents.

Examples of acidifying agents that may be mentioned include mineral or organic acids, for instance hydrochloric acid, orthophosphoric acid, sulphuric acid or acetic acid.

Examples of basifying agents that may be mentioned include aqueous ammonia, alkaline carbonates, alkanolamines such as monoethanolamine, diethanolamine and triethanolamine and derivatives thereof, sodium hydroxide, potassium hydroxide and the compounds of formula (C) below:

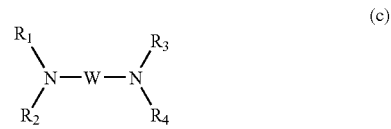

(c)

in which W is a propylene residue optionally substituted with a hydroxyl group or a C$_1$–C$_6$ alkyl radical; R$_1$, R$_2$, R$_3$ and R$_4$, which may be identical or different, represent a hydrogen atom or a C$_1$–C$_6$ alkyl or C$_1$–C$_6$ hydroxyalkyl radical.

The composition in accordance with the invention may also comprise various conventionally used adjuvants, such as anionic, cationic, nonionic, amphoteric or zwitterionic surfactants or mixtures thereof, hair dyes, polymers, mineral thickeners, antioxidants, penetrating agents, fragrances, buffers, dispersants, conditioners, for instance cations, silicones, film-forming agents, preserving agents and stabilizers.

When one or more surfactants are present, preferably of nonionic, anionic or amphoteric type, their content represents from 0.01% to 30% by weight relative to the weight of the composition.

Needless to say, a person skilled in the art will take care to select this or these optional additional compound(s) such that the advantageous properties intrinsically associated with the composition in accordance with the invention are not, or are not substantially, adversely affected by the envisaged addition(s).

The composition according to the invention may be in various forms, such as in the form of liquids, shampoos, creams or gels, or in any other suitable form.

In one form that is particularly preferred according to the present invention, the composition is in the form of a lightening dye shampoo comprising, in a cosmetically acceptable aqueous medium.

The composition according to the invention may also contain at least one oxidizing agent. This agent may be chosen, for example, from hydrogen peroxide, urea peroxide, alkali metal bromates, persalts such as perborates and persulphates, and enzymes such as peroxidases and two-electron or four-electron oxidoreductases. The use of hydrogen peroxide or enzymes is particularly preferred.

A subject of the invention is also the use, for dyeing human keratin materials with a lightening effect, of a composition comprising, in a cosmetically acceptable medium, at least one fluorescent dye soluble in the said medium, and at least one complexing agent chosen from hydroxycarboxylic acids and polycarboxylic acids, and the monovalent or divalent alkali metal, alkaline-earth metal, transition metal, organic amine or ammonium salts thereof, alone or as mixtures.

In the context of this use, the fluorescent compound may be chosen from the fluorescent dyes belonging to the following families: naphthalimides; cationic or non-cationic coumarins; xanthenodi-quinolizines (especially such as sulphorhodamines); azaxanthenes; naphtholactams; azlactones; oxazines; thiazines; dioxazines; monocationic or polycationic fluorescent dyes of azo, azomethine or methine type, alone or as mixtures.

Compounds that may be mentioned more particularly include the compounds of formulae F1, F2 and F3 already detailed previously.

It is similarly possible to use the compounds of structure (F4) below:

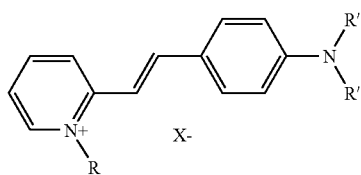

in which formula R represents a methyl or ethyl radical; R' represents a methyl radical and X⁻ represents an anion of chloride, iodide, sulphate, methosulphate, acetate or perchlorate type. An example of a compound of this type that may be mentioned is the photosensitizing dye NK-557 sold by the company Ubichem, for which R represents an ethyl radical, R' represents a methyl radical and X⁻ represents an iodide.

Everything that has been described previously regarding the natures and contents of the various additives present in the composition remains valid and will not be repeated in this section.

According to the present invention, the term "human keratin materials" means the skin, the hair, the nails, the eyelashes and the eyebrows, and more particularly coloured skin and artificially dyed or pigmented hair.

For the purposes of the invention, the term "colored skin" means a skin whose lightness L* measured in the CIEL L*a*b* system is less than or equal to 45 and preferably less than or equal to 40, given that L*=0 is equivalent to black and L*=100 is equivalent to white. The skin types corresponding to this lightness are African skin, Afro-American skin, Hispano-American skin, Indian skin and North African skin.

For the purposes of the invention, the expression "artificially dyed or pigmented hair" means hair whose tone height is less than or equal to 6 (dark blond) and preferably less than or equal to 4 (chestnut-brown).

The lightening of the hair is evaluated by the "tone height", which characterizes the degree or level of lightening. The notion of "tone" is based on the classification of the natural shades, one tone separating each shade from the shade immediately following or preceding it. This definition and the classification of the natural shades are well known to hairstyling professionals and are published in the book "Sciences des traitements capillaires " [Hair treatment sciences] by Charles Zviak, 1988, published by Masson, pp. 215 and 278.

The tone heights range from 1 (black) to 10 (light blond), one unit corresponding to one tone; the higher the figure, the lighter the shade.

Another subject of the present invention thus concerns a process for dyeing human keratin fibres with a lightening effect, which consists in performing the following steps:
  a) the composition according to the invention is applied to the keratin fibres, for a time that is sufficient to develop the desired coloration and lightening,
  b) the said fibres are optionally rinsed,
  c) the said fibres are optionally washed with shampoo and rinsed,
  d) the fibres are dried or are left to dry.

A subject of the present invention is also a process for colouring coloured skin with a lightening effect, in which the composition that has just been described is applied to the skin and the skin is then dried or is left to dry. Preferably, this composition is not used in the presence of an oxidizing agent.

Everything that has been described previously regarding the various constituent components of the composition remains valid, and reference may be made thereto.

In particular, the processes according to the invention are suitable for treating human keratin fibres, and especially artificially dyed or pigmented hair, or alternatively coloured skin.

More particularly, the fibres that may be advantageously treated with the process according to the invention have a tone height of less than or equal to 6 (dark blond) and preferably less than or equal to 4 (chestnut-brown).

Furthermore, a coloured skin capable of being treated in accordance with the invention has a lightness L*, measured in the CIEL L*a*b* system, of less than or equal to 45 and preferably less than or equal to 40.

According to a first embodiment of the invention, the process of dyeing fibres with a lightening effect is performed with a composition that does not comprise oxidizing agent.

According to a second embodiment of the invention, the process of dyeing fibres with a lightening effect is performed with a composition comprising an oxidizing agent.

According to a first variant of these dyeing processes in accordance with the invention, at least one composition as defined above is applied to the fibres, and especially the hair, for a time that is sufficient to develop the desired coloration and lightening, after which the fibres are rinsed, washed optionally with shampoo, rinsed again and dried.

According to a second variant of these dyeing processes in accordance with the invention, at least one composition as defined above is applied to the fibres, and especially the hair, without final rinsing.

According to a third dyeing process variant in accordance with the invention, the dyeing process comprises a preliminary step that consists in separately storing, on the one hand, a composition according to the invention, and, on the other hand, a composition comprising, in a cosmetically acceptable medium, at least one oxidizing agent, and then in mixing them together at the time of use, after which this mixture is applied to the keratin fibres, and especially the hair, for a time that is sufficient to develop the desired coloration, after which the fibres are rinsed, washed optionally with shampoo, rinsed again and dried.

The time required to develop the coloration and to obtain the lightening effect on the fibres, especially the hair, is about 5 to 60 minutes and more particularly about 5 to 40 minutes.

The temperature required to develop the coloration and to obtain the lightening effect is generally between room temperature (15 to 25° C.) and 80° C. and more particularly between 15 and 40° C.

Another subject of the invention is a multi-compartment device for dyeing keratin fibres, and especially the hair, with a lightening effect, comprising at least one compartment containing a composition according to the invention, and at least one other compartment containing a composition comprising at least one oxidizing agent. This device may be equipped with a means for applying the desired mixture to the fibres, such as the devices described in patent FR 2 586 913.

It should be noted that the composition according to the invention, if it is used to treat keratin fibres, for example such as chestnut-brown hair, makes it possible to achieve the following results:

If the reflectance of the hair is measured when it is irradiated with visible light in the wavelength range from 400 to 700 nanometers, and if the reflectance curves as a function of the wavelength are compared for hair treated with the composition of the invention and untreated hair, it is found that the reflectance curve corresponding to the treated hair, in a wavelength range from 500 to 700 nanometers, is higher than that corresponding to the untreated hair.

This means that, in the wavelength range from 500 to 700 nanometers, and preferably from 540 to 700 nanometers, there is at least one range in which the reflectance curve corresponding to the treated hair is higher than the reflectance curve corresponding to the untreated hair. The term "higher than" means a difference of at least 0.05% and preferably of at least 0.1% of reflectance.

However, it is pointed out that there may be, within the wavelength range from 500 to 700 nanometers and preferably from 540 to 700 nanometers, one or more ranges in which the reflectance curve corresponding to the treated fibres is either superimposable on or lower than the reflectance curve corresponding to the untreated fibres.

Preferably, the wavelength at which the difference is maximal between the reflectance curve for the treated hair and that for the untreated hair is in the wavelength range from 500 to 650 nanometers and preferably in the wavelength range from 550 to 620 nanometers.

In addition, and preferably, the composition according to the invention is capable of lightening the hair and the skin to a shade which, measured in the CIEL L*a*b* system, has a variable b* of greater than or equal to 6, with a b*/absolute value of a* ratio of greater than 1.2 according to the selection test described below.

Selection Test

The composition is applied to chestnut-brown keratin fibres, more particularly the hair, at a rate of 10 grams of composition per 1 gram of chestnut-brown fibres. The composition is spread so as to cover all of the fibres. The composition is left to act for 20 minutes at room temperature (20 to 25° C.). The fibres are then rinsed with water and then washed with a shampoo based on lauryl ether sulphate. They are then dried. The spectrocolorimetric characteristics of the fibres are then measured in order to determine the L*a*b* coordinates.

In the CIEL L*a*b* system, a* and b* indicate two colour axes: a* indicates the green/red colour axis (+a* is red, −a* is green) and b* indicates the blue/yellow colour axis (+b* is yellow and −b* is blue); values close to zero for a* and b* correspond to grey shades.

The examples that follow are intended to illustrate the invention without, however, limiting its scope.

EXAMPLES

Fluorescent Compound

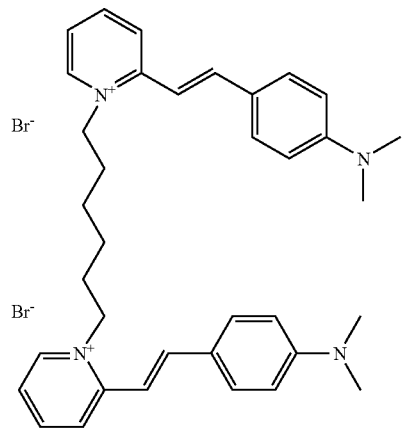

93 g of 2-picoline are reacted with 120 g of 1,6-dibromohexane in dimethylformamide at 110° C. for 5 hours.

The precipitated product is recovered and filtered off.

109 g of the product obtained above are dissolved in methanol and 82.82 g of p-dimethylamino-benzaldehyde are added in two portions, in the presence of pyrrolidine.

The mixture is then left for 30 minutes.

The product is recovered in precipitated form.

Analysis by mass spectroscopy: 266.

Elemental analysis: C, 62.43%; H, 6.40%; Br, 23.07%; N, 8.09%.

The formula is as follows: $C_{36}H_{44}N_4 \cdot 2Br$.

Compositions

| Composition | 1 | 2 |
|---|---|---|
| Fluorescent compound | 1% | 1% |
| Mucic acid | 0.2% | — |
| N-lauroylethylenediamine-N,N',N'-triacetic acid | — | 0.2% |
| pH agent qs | pH 7 | pH 7 |
| Distilled water | qs 100% | qs 100% |

Dyeing

Each composition is applied to a lock of natural chestnut-brown hair (tone height 4) with a leave-in time of 20 minutes.

The lock is then rinsed and dried under a hood for 30 minutes.

A marked lightening effect is obtained on the locks.

The invention claimed is:

1. A composition comprising, in a cosmetically acceptable medium,
at least one fluorescent dye that is soluble in the medium, and
at least one complexing agent chosen from
hydroxycarboxylic acids, or the monovalent alkali metal, divalent alkali metal, alkaline-earth metal, transition metal, organic amine or ammonium salts thereof; and
polycarboxylic acids, or the monovalent alkali metal, divalent alkali metal, alkaline-earth metal, transition metal, organic amine or ammonium salts thereof,
with the proviso that the composition does not comprise, as a fluorescent dye, 2-[2-(4-dialkylamino)phenylethenyl]-1-alkylpyridinium in which the alkyl radical of the pyridinium nucleus is a methyl or ethyl radical and the alkyl radical of the benzene nucleus is a methyl radical, and in which the counterion is a halide; and
wherein the at least one fluorescent dye is chosen from:

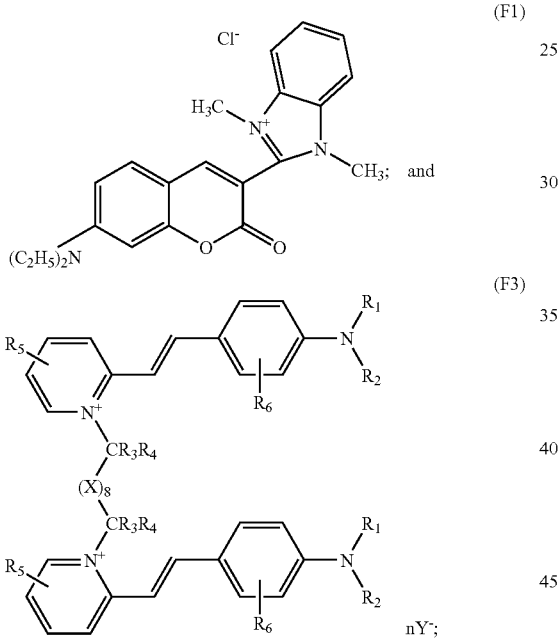

wherein:
$R_1$ and $R_2$, which may be identical or different, are each chosen from:
a hydrogen atom;
linear or branched alkyl radicals comprising 1 to 10 carbon atoms, optionally interrupted and/or substituted with at least one hetero atom and/or group comprising at least one hetero atom and/or substituted with at least one halogen atom;
aryl or arylalkyl radicals, the aryl group comprising 6 carbon atoms and the alkyl radical comprising 1 to 4 carbon atoms; the aryl radical optionally being substituted with at least one linear or branched alkyl radical comprising 1 to 4 carbon atoms optionally interrupted and/or substituted with at least one hetero atom and/or group comprising at least one hetero atom and/or substituted with at least one halogen atom;

$R_1$ and $R_2$ may optionally be linked so as to form a heterocycle with the nitrogen atom and may comprise at least one other hetero atom, the heterocycle optionally being substituted with at least one linear or branched alkyl radical and optionally being interrupted and/or substituted with at least one hetero atom and/or group comprising at least one hetero atom and/or substituted with at least one halogen atom; or
$R_1$ or $R_2$ may optionally be engaged in a heterocycle comprising the nitrogen atom and one of the carbon atoms of the phenyl group bearing the nitrogen atom;
$R_3$ and $R_4$, which may be identical or different, are each chosen from a hydrogen atom and alkyl radical comprising 1 to 4 carbon atoms;
$R_5$, which may be identical or different, is chosen from a hydrogen atom, a halogen atom, and linear or branched alkyl radicals comprising 1 to 4 carbon atoms, optionally interrupted with at least one hetero atom;
$R_6$, which may be identical or different, is chosen from a hydrogen atom; a halogen atom; linear or branched alkyl radicals comprising 1 to 4 carbon atoms, optionally substituted and/or interrupted with at least one hetero atom and/or group bearing at least one hetero atom and/or substituted with at least one halogen atom;
X is chosen from:
linear or branched alkyl radicals comprising 1 to 14 carbon atoms and alkenyl radicals comprising 2 to 14 carbon atoms, optionally interrupted and/or substituted with at least one hetero atom and/or group comprising at least one hetero atom and/or substituted with at least one halogen atom;
5- or 6-membered heterocyclic radicals optionally substituted with at least one linear or branched alkyl radical comprising 1 to 14 carbon atoms, optionally substituted with at least one hetero atom; with at least one linear or branched aminoalkyl radical comprising 1 to 4 carbon atoms, optionally substituted with at least one hetero atom; or with at least one halogen atom;
fused or non-fused aromatic or diaromatic radicals, optionally separated with an alkyl radical comprising 1 to 4 carbon atoms, wherein the aryl radical(s) of the aromatic or diaromatic radicals is optionally substituted with at least one halogen atom or with at least one alkyl radical comprising 1 to 10 carbon atoms optionally substituted and/or interrupted with at least one hetero atom and/or group bearing at least one hetero atom;
dicarbonyl radicals;
the group X optionally bearing one or more cationic charges; a equals 0 or 1;
$Y^-$, which may be identical or different, is chosen from organic or inorganic anions; and
n is an integer at least equal to 2 and at most equal to the number of cationic charges present in the fluorescent compound; and

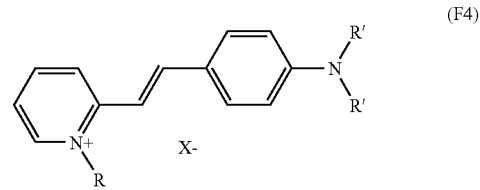

wherein:
R is chosen from a methyl or ethyl radical;
R' is a methyl radical; and
X'' is chosen from chloride, iodide, sulphate, methosulphate, acetate, and perchlorate anions.

2. The composition according to claim 1, wherein the fluorescent dye leads to a reflectance maximum that is in the wavelength range of from 500 to 650 nanometers.

3. The composition according to claim 2, wherein the fluorescent dye leads to a reflectance maximum that is in the wavelength range of from 550 to 620 nanometers.

4. The composition according to claim 1, wherein the at least one fluorescent dye is present in the composition in an amount ranging from 0.01% to 20% by weight relative to the total weight of the composition.

5. The composition according to claim 4, wherein the at least one fluorescent dye is present in the composition in an amount ranging from 0.1% to 5% by weight relative to the total weight of the composition.

6. The composition according to claim 1, wherein the at least one complexing agent is chosen from hydroxycarboxylic acids having the formula:

$$R-(CHOH)_4-CO_2X,$$

in which
R is chosen from a $CH_2OH$ group and a $CO_2X$ group and
X is chosen from a hydrogen, a monovalent cation, and a divalent cation.

7. The composition according to claim 6, wherein the at least one hydroxycarboxylic acid complexing agent is chosen from gluconic acid, mucic acid, glucaric acid, mannaric acid, salts thereof, and mixtures thereof.

8. The composition according to claim 1, wherein the at least one complexing agent is chosen from polycarboxylic acids having the formula:

$$R-N(Y)(CH(R')CO_2X),$$

in which
Y is chosen from a hydrogen atom and a group $CH(R')CO_2X$;
R' is chosen from a hydrogen atom and a group $CH_2CO_2X$;
R is chosen from
a hydrogen atom,
—$CH(CO_2X)$—$(CH_2)_nCO_2X$,
—$(CH_2)OH$,
—$CH(R'')CO_2X$,
—$(CH_2)_n$—$N(COR'')$—$CH_2CO_2X$,
—$(CH_2)_n$—$N(CH_2CO_2X)CH_2CO_2X$, and
—$(CH_2)_nNH$—$CH(CO_2X)CH_2CO_2X$,
in which R'' is chosen from linear or branched $C_1$–$C_{30}$ or cyclic $C_3$–$C_{30}$ alkyl groups and n is an integer ranging from 1 to 5; and
X is chosen from a hydrogen atom, a monovalent cation, and a divalent cation.

9. The composition according to claim 8, wherein the at least one polycarboxylic acid complexing agent is chosen from:
compounds comprising four carboxylic acid or carboxylic salt functions, when R is a hydrogen atom and R' is a group —$CH_2$—$CO_2X$, or when R is a group —$CH(CO_2X)$—$(CH_2)_2$—$CO_2X$ and R' is a hydrogen atom; and
compounds comprising three carboxylic acid or carboxylic salt functions, when R is a group —$CH(CH_3)$—$CO_2X$ and R' is a hydrogen atom, or when R is a group —$(CH_2)_2$—$N(-COR'')$—$CH_2$—$CO_2X$ and R' is a hydrogen atom.

10. The composition according to claim 8, wherein the at least one polycarboxylic acid complexing agent is chosen from methylglycinediacetic acid, N-lauroylethylenediamine-N,N',N'-triacetic acid, iminodisuccinic acid, N,N-dicarboxymethyl-L-glutamic acid, ethylenediamine-N,N'-disuccinic acid, salts thereof, and mixtures thereof.

11. The composition according to claim 1, wherein the at least one complexing agent is present in the composition in an amount ranging from 0.0001% to 20% by weight relative to the weight of the composition.

12. The composition according to claim 11, wherein the at least one complexing agent is present in the composition in an amount ranging from 0.01% to 5% by weight relative to the weight of the composition.

13. The composition according to claim 1, wherein the composition further comprises at least one surfactant chosen from nonionic, anionic and amphoteric surfactants.

14. The composition according to claim 13, wherein the surfactant content is 0.01% to 30% by weight relative to the total weight of the composition.

15. The composition according to claim 1, wherein the composition further comprises at least one oxidizing agent.

16. The composition according to claim 15, wherein the oxidizing agent is chosen from hydrogen peroxide, urea peroxide, alkali metal bromates, persalts, and enzymes.

17. The composition according to claim 16, wherein the oxidizing agent is hydrogen peroxide.

18. A process for dyeing human keratin fibers with a lightening effect, comprising:
a) applying to keratin fibers for a time sufficient to develop coloration and lightening a composition comprising, in a cosmetically acceptable medium,
at least one fluorescent dye that is soluble in the medium, and
at least one complexing agent chosen from
hydroxycarboxylic acids, or the monovalent alkali metal, divalent alkali metal, alkaline-earth metal, transition metal, organic amine or ammonium salts thereof; and
polycarboxylic acids, or the monovalent alkali metal, divalent alkali metal, alkaline-earth metal, transition metal, organic amine or ammonium salts thereof;
with the proviso that the composition does not comprise, as a fluorescent dye, 2-[2-(4-dialkylamino)phenylethenyl]-1-alkylpyridinium in which the alkyl radical of the pyridinium nucleus is a methyl or ethyl radical and the alkyl radical of the benzene nucleus is a methyl radical, and in which the counterion is a halide; and
wherein the at least one fluorescent dye is chosen from:

(F1)

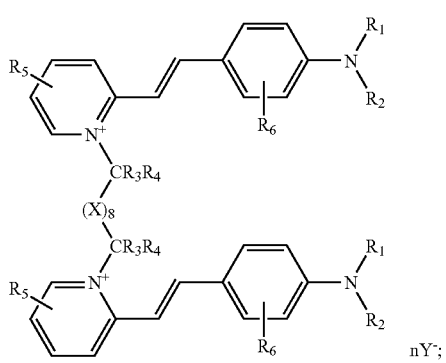

(F3)

wherein:

R₁ and R₂, which may be identical or different, are each chosen from:
- a hydrogen atom;
- linear or branched alkyl radicals comprising 1 to 10 carbon atoms, optionally interrupted and/or substituted with at least one hetero atom and/or group comprising at least one hetero atom and/or substituted with at least one halogen atom;
- aryl or arylalkyl radicals, the aryl group comprising 6 carbon atoms and the alkyl radical comprising 1 to 4 carbon atoms; the aryl radical optionally being substituted with at least one linear or branched alkyl radical comprising 1 to 4 carbon atoms optionally interrupted and/or substituted with at least one hetero atom and/or group comprising at least one hetero atom and/or substituted with at least one halogen atom;
- R₁ and R₂ may optionally be linked so as to form a heterocycle with the nitrogen atom and may comprise at least one other hetero atom, the heterocycle optionally being substituted with at least one linear or branched alkyl radical and optionally being interrupted and/or substituted with at least one hetero atom and/or group comprising at least one hetero atom and/or substituted with at least one halogen atom; or
- R₁ or R₂ may optionally be engaged in a heterocycle comprising the nitrogen atom and one of the carbon atoms of the phenyl group bearing the nitrogen atom;

R₃ and R₄, which may be identical or different, are each chosen from a hydrogen atom and alkyl radicals comprising 1 to 4 carbon atoms;

R₅, which may be identical or different, is chosen from a hydrogen atom, a halogen atom, and linear or branched alkyl radicals comprising 1 to 4 carbon atoms, optionally interrupted with at least one hetero atom;

R₆, which may be identical or different, is chosen from a hydrogen atom; a halogen atom; linear or branched alkyl radicals comprising 1 to 4 carbon atoms, optionally substituted and/or interrupted with at least one hetero atom and/or group bearing at least one hetero atom and/or substituted with at least one halogen atom;

X is chosen from:
- linear or branched alkyl radicals comprising 1 to 14 carbon atoms and alkenyl radicals comprising 2 to 14 carbon atoms, optionally interrupted and/or substituted with at least one hetero atom and/or group comprising at least one hetero atom and/or substituted with at least one halogen atom;
- 5- or 6-membered heterocyclic radicals optionally substituted with at least one linear or branched alkyl radical comprising 1 to 14 carbon atoms, optionally substituted with at least one hetero atom; with at least one linear or branched aminoalkyl radical comprising 1 to 4 carbon atoms, optionally substituted with at least one hetero atom; or with at least one halogen atom;
- fused or non-fused aromatic or diaromatic radicals, optionally separated with an alkyl radical comprising 1 to 4 carbon atoms, wherein the aryl radical(s) of the aromatic or diaromatic radicals is optionally substituted with at least one halogen atom or with at least one alkyl radical comprising 1 to 10 carbon atoms optionally substituted and/or interrupted with at least one hetero atom and/or group bearing at least one hetero atom;
- dicarbonyl radicals;
- the group X optionally bearing one or more cationic charges;

a equals 0 or 1;

Y⁻, which may be identical or different, is chosen from organic or inorganic anions; and n is an integer at least equal to 2 and at most equal to the number of cationic charges present in the fluorescent compound; and

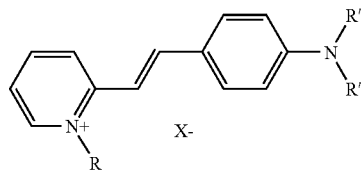

(F4)

wherein:

R is chosen from a methyl or ethyl radical;

R' is a methyl radical; and

X⁻ is chosen from chloride, iodide, sulphate, methosulphate, acetate, and perchlorate anions;

b) optionally rinsing the fibers;

c) optionally washing the fibers with shampoo and rinsing again; and d) drying the fibers or leaving the fibers to dry.

19. The process according to claim 18, wherein, prior to application of the dyeing composition, the human keratin fibers have previously been artificially dyed or pigmented.

20. The process according to claim 18, wherein the human keratin fibers are hair with a tone height of less than or equal to 6.

21. The process according to claim 20, wherein the hair has a tone height of less than or equal to 4.

22. The process according to claim 18, wherein the fluorescent dye leads to a reflectance maximum that is in the wavelength range from 500 to 650 nanometers.

23. The process according to claim 22, wherein the fluorescent dye leads to a reflectance maximum that is in the wavelength range from 550 to 620 nanometers.

24. A process for dyeing human keratin fibers with a lightening effect, comprising:

a) separately storing:
- at least one first composition comprising, in a cosmetically acceptable medium,
  - at least one fluorescent dye that is soluble in the medium, and at least one complexing agent chosen from
hydroxycarboxylic acids, or the monovalent alkali metal, divalent alkali metal, alkaline-earth metal, transition metal, organic amine or ammonium salts thereof; and
polycarboxylic acids, or the monovalent alkali metals, divalent alkali metal, alkaline-earth metal, transition metal, organic amine or ammonium salts thereof;
with the proviso that the composition does not comprise, as a fluorescent dye, 2-[2-(4-dialkylamino) phenylethenyl]-1-alkylpyridinium in which the alkyl radical of the pyridinium nucleus is a methyl or ethyl radical and the alkyl radical of the benzene nucleus is a methyl radical, and in which the counterion is a halide; and
wherein the at least one fluorescent dye is chosen from:

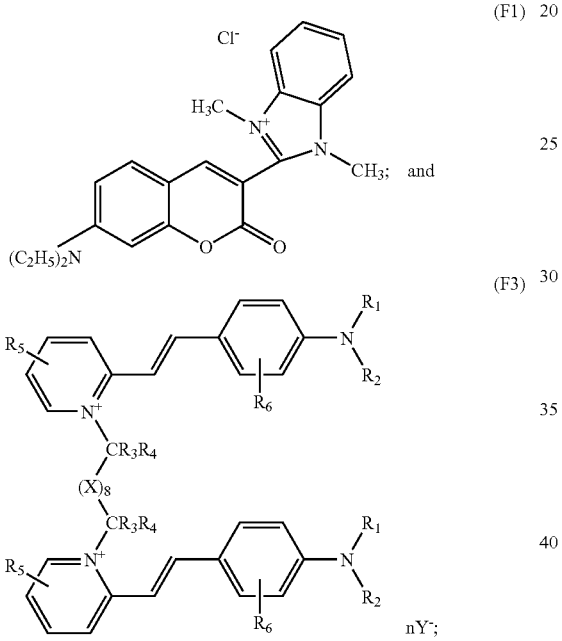

wherein:

$R_1$ and $R_2$, which may be identical or different, each are chosen from:
  a hydrogen atom;
  linear or branched alkyl radicals comprising 1 to 10 carbon atoms, optionally interrupted and/or substituted with at least one hetero atom and/or group comprising at least one hetero atom and/or substituted with at least one halogen atom;
  aryl or arylalkyl radicals, the aryl group comprising 6 carbon atoms and the alkyl radical comprising 1 to 4 carbon atoms; the aryl radical optionally being substituted with at least one linear or branched alkyl radical comprising 1 to 4 carbon atoms optionally interrupted and/or substituted with at least one hetero atom and/or group comprising at least one hetero atom and/or substituted with at least one halogen atom;
$R_1$ and $R_2$ may optionally be linked so as to form a heterocycle with the nitrogen atom and may comprise at least one other hetero atom, the heterocycle optionally being substituted with at least one linear or branched alkyl radical and optionally being interrupted and/or substituted with at least one hetero atom and/or group comprising at least one hetero atom and/or substituted with at least one halogen atom; or
$R_1$ and $R_2$ may optionally be engaged in a heterocycle comprising the nitrogen atom and one of the carbon atoms of the phenyl group bearing the nitrogen atom;
$R_3$ and $R_4$, which may be identical or different, are each chosen from a hydrogen atom and alkyl radicals comprising 1 to 4 carbon atoms;
$R_5$, which may be identical or different, is chosen from a hydrogen atom, a halogen atom, and linear or branched alkyl radicals comprising 1 to 4 carbon atoms, optionally interrupted with at least one hetero atom;
$R_6$, which may be identical or different, is chosen from a hydrogen atom; a halogen atom; linear or branched alkyl radicals comprising 1 to 4 carbon atoms, optionally substituted and/or interrupted with at least one hetero atom and/or group bearing at least one hetero atom and/or substituted with at least one halogen atom;
X is chosen from:
  linear or branched alkyl radicals comprising 1 to 14 carbon atoms and alkenyl radicals comprising 2 to 14 carbon atoms, optionally interrupted and/or substituted with at least one hetero atom and/or group comprising at least one hetero atom and/or substituted with at least one halogen atom;
  5- or 6-membered heterocyclic radicals optionally substituted with at least one linear or branched alkyl radical comprising 1 to 14 carbon atoms, optionally substituted with at least one hetero atom; with at least one linear or branched aminoalkyl radical comprising 1 to 4 carbon atoms, optionally substituted with at least one hetero atom; or with at least one halogen atom;
  fused or non-fused aromatic or diaromatic radicals, optionally separated with an alkyl radical comprising 1 to 4 carbon atoms, wherein the aryl radical(s) of the aromatic or diaromatic radicals is optionally substituted with at least one halogen atom or with at least one alkyl radical comprising 1 to 10 carbon atoms optionally substituted and/or interrupted with at least one hetero atom and/or group bearing at least one hetero atom;
  dicarbonyl radicals;
  the group X optionally bearing one or more cationic charges;
a equals 0 or 1;
$Y^-$, which may be identical or different, is chosen from organic or inorganic anions; and
n is an integer at least equal to 2 and at most equal to the number of cationic charges present in the fluorescent compound; and

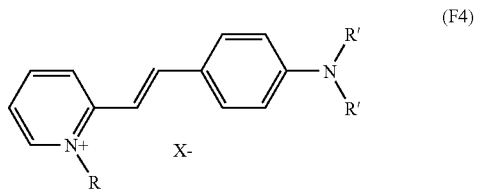

wherein:
R is chosen from a methyl or ethyl radical;
R' is a methyl radical; and X" is chosen from chloride, iodide, sulphate, methosulphate, acetate, and perchlorate anions; and at least one second composition comprising, in a cosmetically acceptable medium, at least one oxidizing agent;

b) mixing together the at least one first and at least one second compositions and applying the mixture to the keratin fibers for a time sufficient to develop coloration and lightening, wherein the at least one first and at least one second compositions are mixed only at the time of application to the keratin fibers;

c) rinsing the fibers;

d) optionally washing the fibers with shampoo and rinsing; and e) drying the fibers or leaving the fibers to dry.

25. The process according to claim 24, wherein prior to application of the dyeing composition, the human keratin fibers have previously been artificially dyed or pigmented.

26. The process according to claim 24, wherein the human keratin fibers are hair with a tone height of less than or equal to 6.

27. The process according to claim 26, wherein the hair has a tone height of less than or equal to 4.

28. The process according to claim 24, wherein the fluorescent dye leads to a reflectance maximum that is in the wavelength range from 500 to 650 nanometers.

29. The process according to claim 28, wherein the fluorescent dye leads to a reflectance maximum that is in the wavelength range from 550 to 620 nanometers.

30. A process for coloring colored skin with a lightening effect, comprising:

a) applying to the skin a composition comprising, in a cosmetically acceptable medium, at least one fluorescent dye that is soluble in the medium, and at least one complexing agent chosen from hydroxycarboxylic acids, or the monovalent alkali metal, divalent alkali metal, alkaline-earth metal, transition metal, organic amine or ammonium salts thereof; and polycarboxylic acids, or the monovalent alkali metal, divalent alkali metal, alkaline-earth metal, transition metal, organic amine or ammonium salts thereof;

with the proviso that the composition does not comprise, as a fluorescent dye, 2-[2-(4-dialkylamino)phenylethenyl]-1-alkylpyridinium in which the alkyl radical of the pyridinium nucleus is a methyl or ethyl radical and the alkyl radical of the benzene nucleus is a methyl radical, and in which the counterion is a halide; and wherein the at least one fluorescent dye is chosen from:

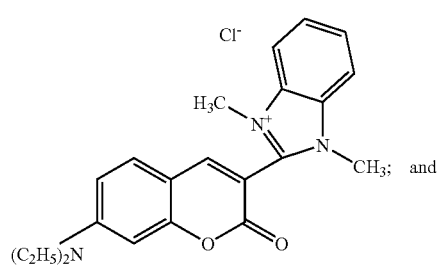

(F1)

and

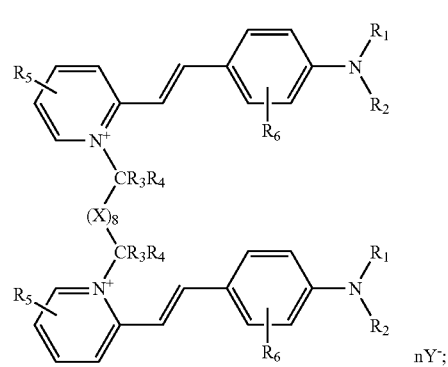

(F3)

wherein:

$R_1$ and $R_2$, which may be identical or different, are each chosen from:

a hydrogen atom;

linear or branched alkyl radicals comprising 1 to 10 carbon atoms, optionally interrupted and/or substituted with at least one hetero atom and/or group comprising at least one hetero atom and/or substituted with at least one halogen atom;

aryl or arylalkyl radicals, the aryl group comprising 6 carbon atoms and the alkyl radical comprising 1 to 4 carbon atoms; the aryl radical optionally being substituted with at least one linear or branched alkyl radical comprising 1 to 4 carbon atoms optionally interrupted and/or substituted with at least one hetero atom and/or group comprising at least one hetero atom and/or substituted with at least one halogen atom;

$R_1$ and $R_2$ may optionally be linked so as to form a heterocycle with the nitrogen atom and may comprise at least one other hetero atom, the heterocycle optionally being substituted with at least one linear or branched alkyl radical and optionally being interrupted and/or substituted with at least one hetero atom and/or group comprising at least one hetero atom and/or substituted with at least one halogen atom; or $R_1$ or $R_2$ may optionally be engaged in a heterocycle comprising the nitrogen atom and one of the carbon atoms of the phenyl group bearing the nitrogen atom;

$R_3$ and $R_4$, which may be identical or different, are each chosen from a hydrogen atom and alkyl radicals comprising 1 to 4 carbon atoms;

$R_5$, which may be identical or different, is chosen from a hydrogen atom, a halogen atom, and linear or branched alkyl radicals comprising 1 to 4 carbon atoms, optionally interrupted with at least one hetero atom;

$R_6$, which may be identical or different, is chosen from a hydrogen atom; a halogen atom; linear or branched alkyl radicals comprising 1 to 4 carbon atoms, optionally substituted and/or interrupted with at least one hetero atom and/or group bearing at least one hetero atom and/or substituted with at least one halogen atom;

X is chosen from:

linear or branched alkyl radicals comprising 1 to 14 carbon atoms, and alkenyl radicals comprising 2 to 14 carbon atoms, optionally interrupted and/or substituted with at least one hetero atom and/or group comprising at least one hetero atom and/or substituted with at least one halogen atom;

5- or 6-membered heterocyclic radicals optionally substituted with at least one linear or branched alkyl radical comprising 1 to 14 carbon atoms, optionally substituted with at least one hetero atom; with at least one linear or branched aminoalkyl radical comprising 1 to 4 carbon atoms, optionally substituted with at least one hetero atom; or with at least one halogen atom;

fused or non-fused aromatic or diaromatic radicals, optionally separated with an alkyl radical comprising 1 to 4 carbon atoms, wherein the aryl radical(s) of the aromatic or diaromatic radicals is optionally substituted with at least one halogen atom or with at least one alkyl radical comprising 1 to 10 carbon atoms optionally substituted and/or interrupted with at least one hetero atom and/or group bearing at least one hetero atom;

dicarbonyl radicals;

the group X optionally bearing one or more cationic charges; a equals 0 or 1;

Y⁻, which may be identical or different, is chosen from organic or inorganic anions; and n is an integer at least equal to 2 and at most equal to the number of cationic charges present in the fluorescent compound; and

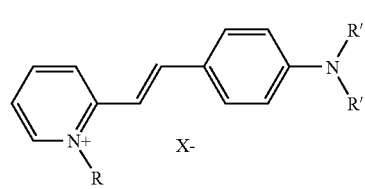

wherein:
R is chosen from a methyl or ethyl radical;
R' is a methyl radical; and
X'' is chosen from chloride, iodide, sulphate, methosulphate, acetate, and perchlorate anions; and
b) drying the skin or leaving the skin to dry.

31. A multi-compartment device for dyeing and lightening keratin fibers, comprising:
at least one compartment containing a composition comprising, in a cosmetically acceptable medium,
at least one fluorescent dye that is soluble in the medium, and
at least one complexing agent chosen from
hydroxycarboxylic acids, or the monovalent alkali metal, divalent alkali metal, alkaline-earth metal, transition metal, organic amine or ammonium salts thereof; and
polycarboxylic acids, or the monovalent alkali metal, divalent alkali metal, alkaline-earth metal, transition metal, organic amine or ammonium salts thereof;
with the proviso that the composition does not comprise, as a fluorescent dye, 2-[2-(4-dialkylamino)phenylethenyl]-1-alkylpyridinium in which the alkyl radical of the pyridinium nucleus is a methyl or ethyl radical and the alkyl radical of the benzene nucleus is a methyl radical, and in which the counterion is a halide; and
wherein the at least one fluorescent dye is chosen from;

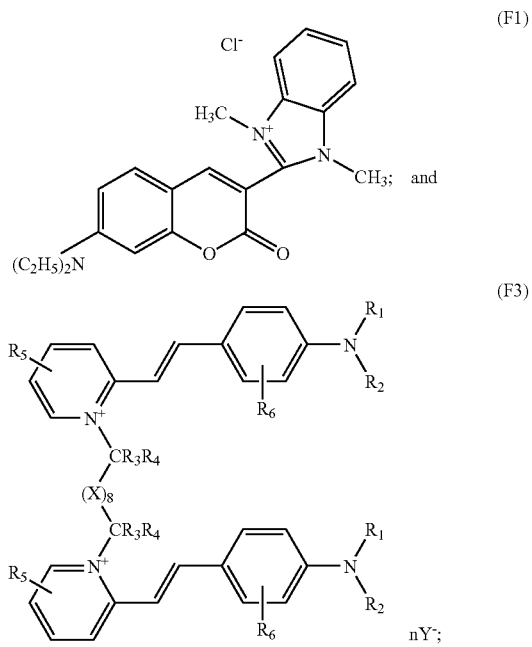

wherein:
$R_1$ and $R_2$, which may be identical or different, are each chosen from:
a hydrogen atom;
linear or branched alkyl radicals comprising 1 to 10 carbon atoms, optionally interrupted and/or substituted with at least one hetero atom and/or group comprising at least one hetero atom and/or substituted with at least one halogen atom;
aryl or arylalkyl radicals, the aryl group comprising 6 carbon atoms and the alkyl radical comprising 1 to 4 carbon atoms; the aryl radical optionally being substituted with at least one linear or branched alkyl radical comprising 1 to 4 carbon atoms optionally interrupted and/or substituted with at least one hetero atom and/or group comprising at least one hetero atom and/or substituted with at least one halogen atom;
$R_1$ and $R_2$ may optionally be linked so as to form a heterocycle with the nitrogen atom and may comprise at least one other hetero atom, the heterocycle optionally being substituted with at least one linear or branched alkyl radical and optionally being interrupted and/or substituted with at least one hetero atom and/or group comprising at least one hetero atom and/or substituted with at least one halogen atom; or
$R_1$ or $R_2$ may optionally be engaged in a heterocycle comprising the nitrogen atom and one of the carbon atoms of the phenyl group bearing the nitrogen atom;
$R_3$ and $R_4$, which may be identical or different, are each chosen from a hydrogen atom and alkyl radicals comprising 1 to 4 carbon atoms;
$R_5$, which may be identical or different, is chosen from a hydrogen atom, a halogen atom, and linear or branched alkyl radicals comprising 1 to 4 carbon atoms, optionally interrupted with at least one hetero atom;
$R_6$, which may be identical or different, is chosen from a hydrogen atom; a halogen atom; linear or branched alkyl radicals comprising 1 to 4 carbon atoms, optionally substituted and/or interrupted with at least one hetero atom and/or group bearing at least one hetero atom and/or substituted with at least one halogen atom;

X is chosen from:
- linear or branched alkyl radicals comprising 1 to 14 carbon atoms and alkenyl radicals comprising 2 to 14 carbon atoms, optionally interrupted and/or substituted with at least one hetero atom and/or group comprising at least one hetero atom and/or substituted with at least one halogen atom;
- 5- or 6-membered heterocyclic radicals optionally substituted with at least one linear or branched alkyl radical comprising 1 to 14 carbon atoms, optionally substituted with at least one hetero atom; with at least one linear or branched aminoalkyl radical comprising 1 to 4 carbon atoms, optionally substituted with at least one hetero atom; or with at least one halogen atom;
- fused or non-fused aromatic or diaromatic radicals, optionally separated with an alkyl radical comprising 1 to 4 carbon atoms, wherein the aryl radical(s) of the aromatic or diaromatic radicals is optionally substituted with at least one halogen atom or with at least one alkyl radical comprising 1 to 10 carbon atoms optionally substituted and/or interrupted with at least one hetero atom and/or group bearing at least one hetero atom;
- dicarbonyl radicals;

the group X optionally bearing one or more cationic charges;

a equals 0 or 1;

$Y^-$, which may be identical or different, is chosen from organic or inorganic anions; and n is an integer at least equal to 2 and at most equal to the number of cationic charges present in the fluorescent compound; and

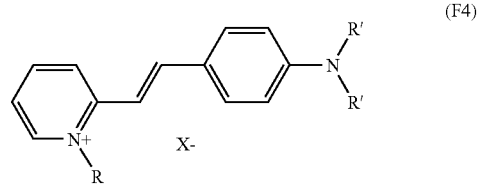

(F4)

wherein:
- R is chosen from a methyl or ethyl radical;
- R' is a methyl radical; and
- X" is chosen from chloride, iodide, sulphate, methosulphate, acetate, and perchlorate anions; and at least one other compartment containing a composition comprising, in a cosmetically acceptable medium, at least one oxidizing agent.

* * * * *

UNITED STATES PATENT AND TRADEMARK OFFICE
CERTIFICATE OF CORRECTION

PATENT NO. : 7,192,454 B2 Page 1 of 6
APPLICATION NO. : 10/814585
DATED : March 20, 2007
INVENTOR(S) : Grégory Plos and Luc Gourlaouen It is certified that error appears in the above-identified patent and that said Letters Patent is hereby corrected as shown below:

In claim 1, column 19, lines 34-47, in the structure for (F3):

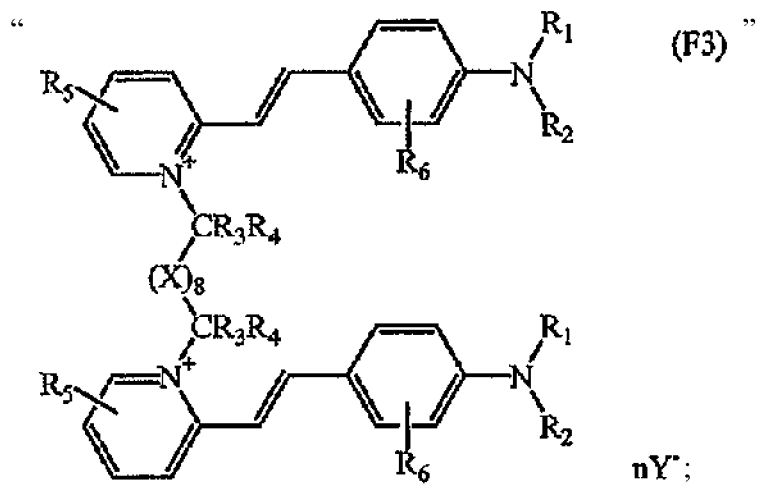

should read

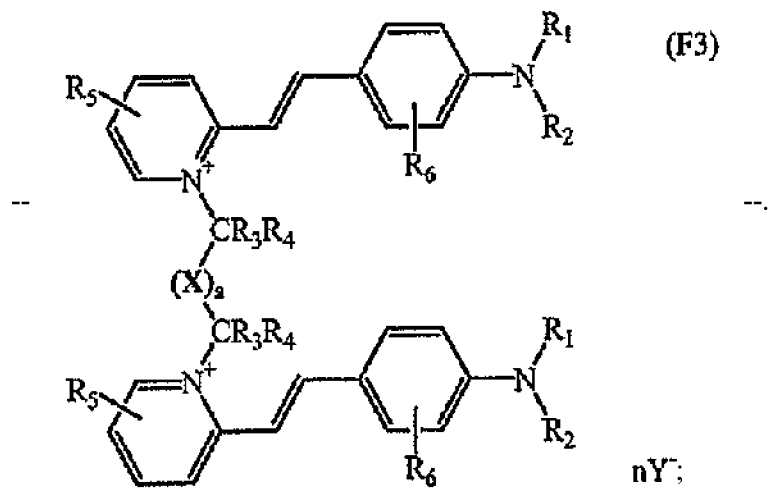

In claim 1, column 20, line 13, "alkyl radical" should read --alkyl radicals--.

In claim 1, column 21, line 4, "X" is" should read --X⁻ is--.

UNITED STATES PATENT AND TRADEMARK OFFICE
CERTIFICATE OF CORRECTION

PATENT NO. : 7,192,454 B2
APPLICATION NO. : 10/814585
DATED : March 20, 2007
INVENTOR(S) : Grégory Plos and Luc Gourlaouen It is certified that error appears in the above-identified patent and that said Letters Patent is hereby corrected as shown below:

In claim 18, column 23, lines 3-16, in the structure for (F3):

"
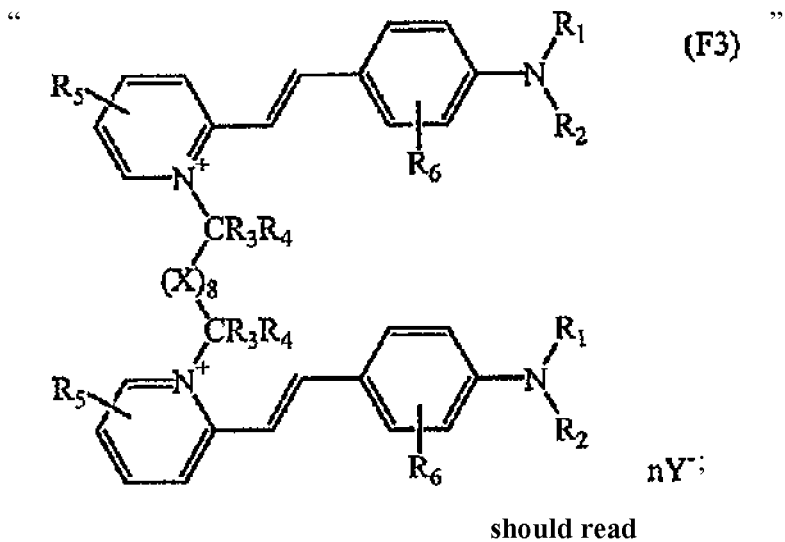
"

should read

--
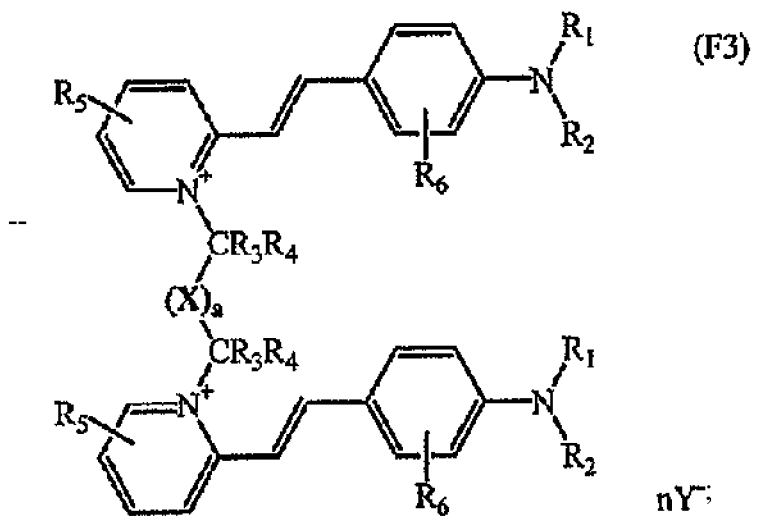
--.

In claim 18, column 24, line 21, "0 or 1:" should read --0 or 1;--.

UNITED STATES PATENT AND TRADEMARK OFFICE
CERTIFICATE OF CORRECTION

PATENT NO. : 7,192,454 B2
APPLICATION NO. : 10/814585
DATED : March 20, 2007
INVENTOR(S) : Grégory Plos and Luc Gourlaouen It is certified that error appears in the above-identified patent and that said Letters Patent is hereby corrected as shown below:

In claim 24, column 25, lines 30-43, in the structure for (F3):

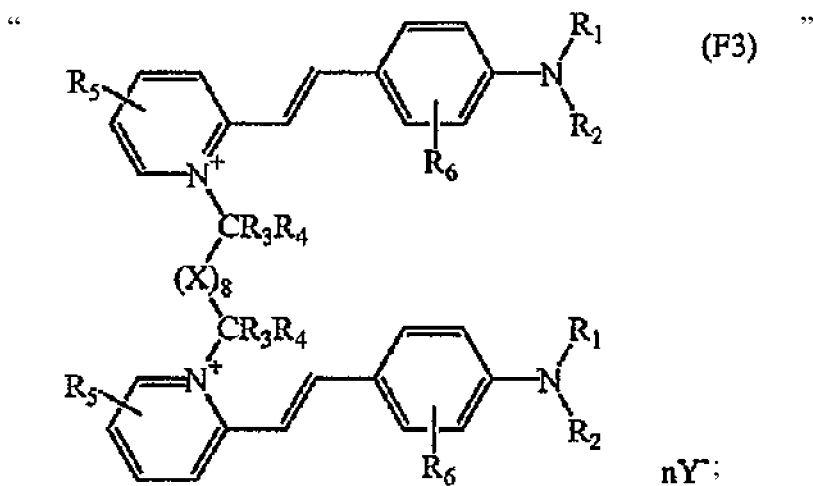

should read

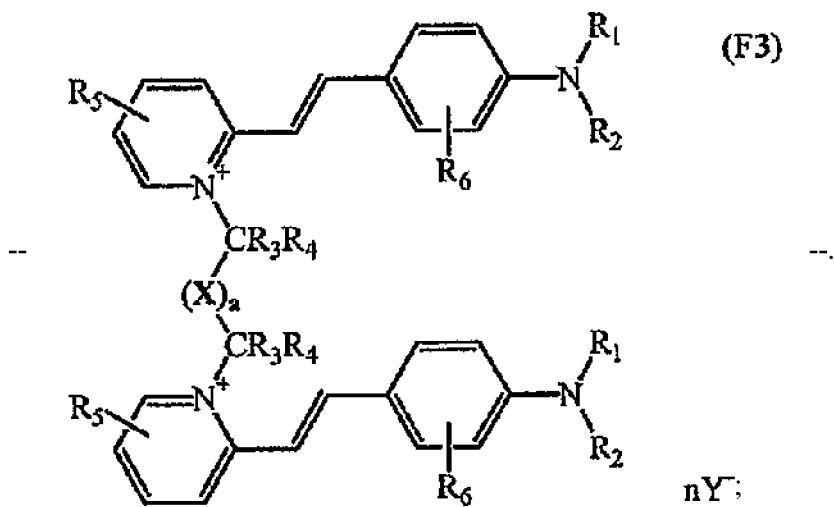

In claim 24, column 27, line 1, "X" is" should read --$X^-$ is--.

UNITED STATES PATENT AND TRADEMARK OFFICE
CERTIFICATE OF CORRECTION

PATENT NO. : 7,192,454 B2
APPLICATION NO. : 10/814585
DATED : March 20, 2007
INVENTOR(S) : Grégory Plos and Luc Gourlaouen It is certified that error appears in the above-identified patent and that said Letters Patent is hereby corrected as shown below:

In claim 30, column 28, lines 3-16, in the structure for (F3):

"
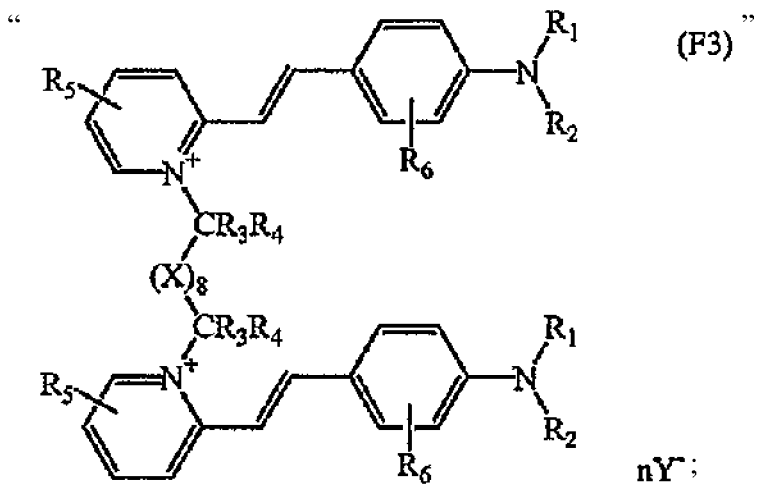
"

should read

--
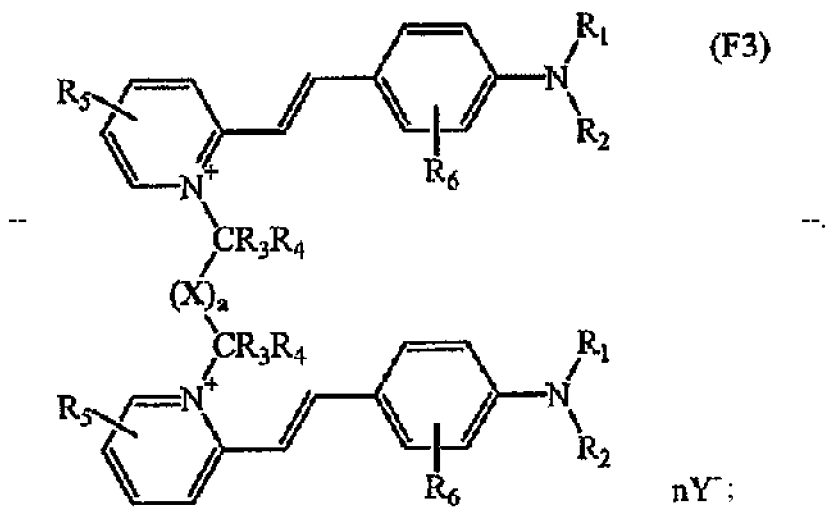
--.

In claim 30, column 28, line 63, after "carbon atoms", delete the comma.

In claim 30, column 29, line 41, "X" is" should read --X⁻ is--.

UNITED STATES PATENT AND TRADEMARK OFFICE
CERTIFICATE OF CORRECTION

PATENT NO. : 7,192,454 B2  
APPLICATION NO. : 10/814585  
DATED : March 20, 2007  
INVENTOR(S) : Grégory Plos and Luc Gourlaouen It is certified that error appears in the above-identified patent and that said Letters Patent is hereby corrected as shown below:

In claim 31, column 29, line 67, "from;" should read --from:--.

In claim 31, column 30, lines 13-26, in the structure for (F3):

"
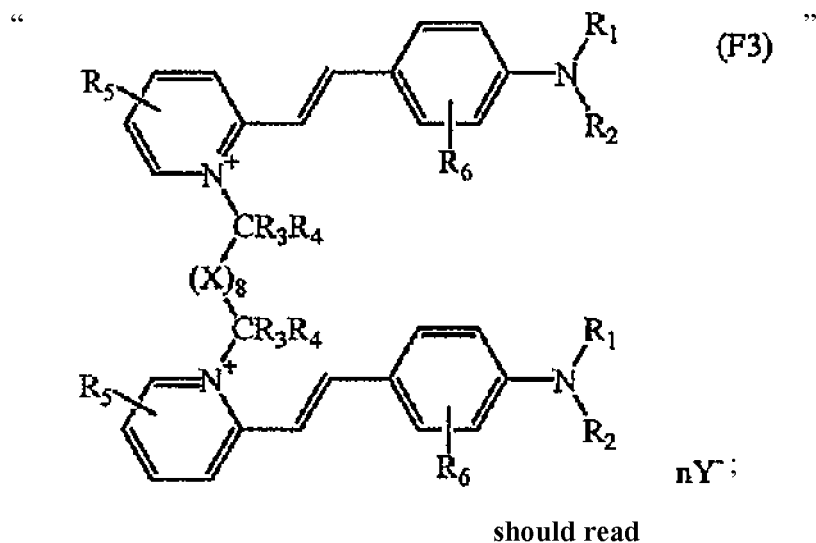
"

should read

--
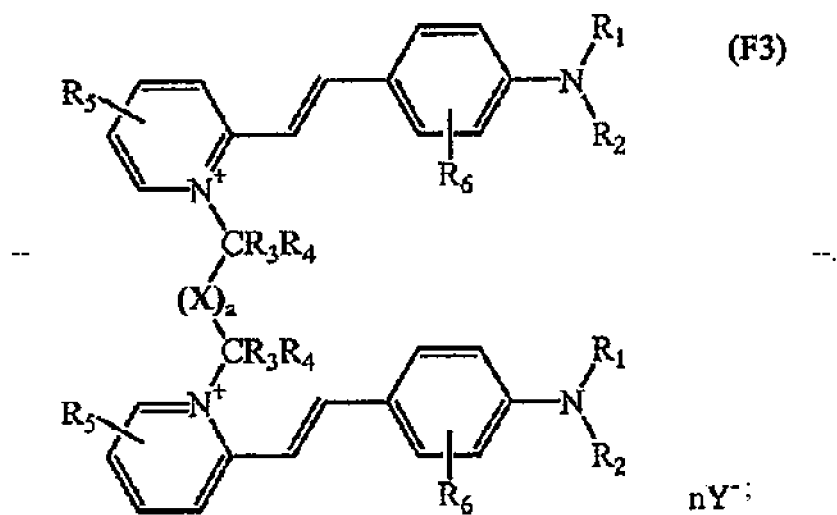
--.

UNITED STATES PATENT AND TRADEMARK OFFICE
CERTIFICATE OF CORRECTION

PATENT NO. : 7,192,454 B2
APPLICATION NO. : 10/814585
DATED : March 20, 2007
INVENTOR(S) : Grégory Plos and Luc Gourlaouen It is certified that error appears in the above-identified patent and that said Letters Patent is hereby corrected as shown below:

In claim 31, column 32, line 22, "X" is" should read --X⁻ is--.

Signed and Sealed this

Tenth Day of July, 2007

JON W. DUDAS
*Director of the United States Patent and Trademark Office*